US005637682A

United States Patent [19]
Nieuwlandt et al.

[11] Patent Number: 5,637,682
[45] Date of Patent: Jun. 10, 1997

[54] HIGH-AFFINITY OLIGONUCLEOTIDE LIGANDS TO THE TACHYKININ SUBSTANCE P

[75] Inventors: Dan T. Nieuwlandt; Larry Gold; Matthew Wecker, all of Boulder, Colo.

[73] Assignee: NeXstar Pharmaceuticals, Inc., Boulder, Colo.

[21] Appl. No.: 441,591

[22] Filed: May 16, 1995

Related U.S. Application Data

[63] Continuation of Ser. No. 303,362, Sep. 9, 1994, which is a continuation-in-part of Ser. No. 714,131, Jun. 10, 1991, Pat. No. 5,475,096, Ser. No. 931,473, Aug. 17, 1992, Pat. No. 5,270,163, Ser. No. 964,624, Oct. 21, 1992, Pat. No. 5,496,938, and Ser. No. 117,991, Sep. 8, 1993, said Ser. No. 714,131, Jun. 10, 1991, Pat. No. 5,475,096, is a continuation-in-part of Ser. No. 536,428, Jun. 11, 1990, abandoned.

[51] Int. Cl.$^6$ .................. C07H 21/02; C07H 21/04; C12Q 1/68; C12P 19/34
[52] U.S. Cl. .............. 536/22.1; 435/6; 435/91.2; 935/77; 935/78
[58] Field of Search .................. 435/6, 91.2; 536/22.1; 935/77, 78

[56] References Cited

U.S. PATENT DOCUMENTS

| | | |
|---|---|---|
| 5,118,672 | 6/1992 | Schinazi et al. . |
| 5,270,163 | 12/1993 | Gold et al. .................. 435/6 |

FOREIGN PATENT DOCUMENTS

| | | |
|---|---|---|
| 2183661 | 6/1987 | United Kingdom . |
| WO89/06694 | 7/1989 | WIPO . |
| WO91/19813 | 12/1991 | WIPO . |
| WO92/03568 | 3/1992 | WIPO . |
| 9214843 | 9/1992 | WIPO .................. 435/6 |

OTHER PUBLICATIONS

Fan et al. (1993) Brit. J. Pharmacology 110:43.
Fox and Woese (1975) Nature 256:505.
Huston et al. (1993) Psychopharmacology 112:147.
Noller and Woese (1981) Science 212:403.
Hobbs et al. (1973) Biochemistry 12:5138.
Guschlbauer et al. (1977) Nucleic Acids Res. 4:1933.
Shibahara et al. (1987) Nucleic Acids Res. 15:4403.
Pieken et al. (1991) Science 253:314.
Tuerk and Gold (1990) Sceince 249:505.
Cadwell and Joyce (1992) PCR Methods Appl. 2:28.
Bartel and Szostak (1993) Science 261:1411.
Leung et al. (1989) Technique 1:11.
Rosen et al. (1980) Biochemistry 19:5687.
Karush and Sonnenberg (1949) J. Amer. Chem. Society 71:1369.
Chassaing et al. (1986) Eur. J. Biochem. 154:77.
Presta and Rose (1988) Science 240:1632.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, N.Y., p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Hobbs et al., Biochemistry 12(25):5138–5145 (1973).

*Primary Examiner*—Stephanie W. Zitomer
*Attorney, Agent, or Firm*—Swanson & Bratschun, LLC

[57] ABSTRACT

Methods are described for the identification and preparation of nucleic acid ligands to Substance P (SP). Included in the invention are specific RNA ligands to SP identified by the SELEX method.

7 Claims, 10 Drawing Sheets

OLIGONUCLEOTIDES

Starting ssDNA template (experiment A):

5'- GCCGGATCCGGGCCTCATGTCGAA [-60N-] TTGAGCGTTTATTCTGAGCTCCC -3'     (SEQ ID NO: 1)

5' PCR Primer:
    Hind III
    5'- CCGAAGCTT<u>AATACGACTCACTATA</u>GGGAGCTCAGAATAAACGCTCAA -3'     (SEQ ID NO: 2)
              T7 Promoter

3' PCR Primer:
    Bam HI
    5'- GCCGGATCCGGGCCTCATGTCGAA -3'     (SEQ ID NO: 3)

Starting RNA (experiment A):

5'- GGGAGCUCAGAAUAAACGCUCAA [-60N-] UUCGACAUGAGGCCCGGAUCCGGC -3'     (SEQ ID NO: 4)

Starting RNA (experiment B, ligand A13):

5'- GGGAGCUCAGAAUAAACGCUCAAGGGCAACGCGGGCACCCCGACAGGUGCAAAAA
        CGCACCGACGCCCGGCCGAAGAAGGGGAUUCGACAUGAGGCCCGGAUCCGGC -3'     (SEQ ID NO: 5)

PEPTIDES

SP:
    N-Arg-Pro-Lys-Pro-Gln-Gln-Phe-Phe-Gly-Leu-Met-NH2     (SEQ ID NO: 6)

Cys-SP:
    Ac-Arg-Pro-Lys-Pro-Gln-Gln-Phe-Phe-Gly-Leu-Met-Cys-C     (SEQ ID NO: 7)

Cys-rSP:
    N-Cys-Met-Leu-Gly-Phe-Phe-Gln-Gln-Pro-Lys-Pro-Arg-C     (SEQ ID NO: 8)

FIGURE 1

```
5'-GGGAGCUCAGAAUAAACGCUCAA----[60N]----UUCGACAUGAGGCCCGGAUCCGGC-3'
```

| Sequence Number | | SEQ ID NO: |
|---|---|---|
| | Group 1 | |
| A1(5) | GAACAAGAUGGCAGUAACGCAACCCAGACAGGAAAAAAA   CCCGACGCGCAAAAA  CAACGGA | 9 |
| A2(1) | ·G                                                                  A | 10 |
| A3(1) | A                            AA              A | 11 |
| | Group 2 | |
| A4(7) | GAAGCGAAAACAGAGGCGAGAGGAAACCUAAAAACAGCGACGAAGCGGCCACUGGUAUCUC | 12 |
| A5(2) | U | 13 |
| A6(1) | G                                         U | 14 |
| A7(1) | U | 15 |
| A8(1) | A | 16 |
| A9(1) | C | 17 |
| | Group 3 | |
| A10(4) | CGCACGACGCACCGUUACAGGGGGGGAAGAA  CCAACCCGAGCGCACGACGGACCGACGC | 18 |
| A11(2) | A G | 19 |
| A12(1) | A   G | 20 |
| | Group 4 | |
| A13(1) | GGGCAACGCGGGCACCCCGACAGGUGCAAAAACGCACCGACGCCCGGCCGAAGAAGGGGA | 5 |
| A14(1) | A                        - | 21 |
| | Group 5 | |
| A15(1) | GCGAAAAGACGAAAAAAACCGACGACACUAGCGCGAUUCGGAAGACUAGCAACAACGACAC | 22 |
| A16(1) | AAGGAAGAAAACAGCAUAAUUAGGCAAAAAGACAAAAACAACAAAUAAAGAAAGAGCAUA | 23 |
| A17(1) | ACAAAAAACAAACGAAAACAUAAAAAUAAAAUUAAAGUAGAAGCGCAAAGAUUAUUACAA | 24 |
| A18(1) | AACUCAAUAUAAAGAAAACGACAAAAACAGAAUGAAGCCAAGAAAACAUACAAGAACGAAGC | 25 |

FIGURE 2

CLASS 1

5'-GGGAGCUCAGAAUAAACGCUCAA--[60N]--UUCGACAUGAGGCCCGAUCCGGC-3'

| Sequence Number | 1 | 10 | 20 | 30 | 40 | 50 | 60 | Kd(µM)² | SEQ ID NO: |
|---|---|---|---|---|---|---|---|---|---|
| B13 | CAAG | CAAGGCAUG | CAAACCUUAGGUC | ACAAA | GAACCGAUGAGGCUGU | CC GG CA | CUUCA | 2.0 | 26 |
| B14 | CCAAA | CUAGGCUAU | GGAAACCUUAGGCU | AAUAA | AGCCAAUGAGCCAU | CCAGGU A | CUUC | >2 | 27 |
| B15 | GAGACCU | GGCAAUGU | GAAACCUUAGGAU | ACAUA | AUCCAAUGAGACCAU | CC GGUCA | CUUCA | 0.65 | 28 |
| B16 | CGCUCC | GCAGUUA | GAAACCUUAGGUU | AUUA | GACCAAUGAUGCCAU | CC GGCCA | CAACU | 0.34 | 29 |
| B18 | CCUCU | GGCAGUGU | GAAACCUUAGGUC | AUUAC | GACCAAUGANGCUAU | CCAGGU A | CUUCA | 0.52 | 30 |
| B20 | CGCUCU | GGCUGUGU | GAAACCUUAGGUU | ACAAAA | ACCAAUGACGCCAU | CUGGACAA | UUCA | >2 | 31 |
| B24 | CCAACA | GGCUAUUG | GAAACCUUAGGUU | AUAAC | GACCAAUGAGCCCGU | CCAGGU | CAUCU | >2 | 32 |
| B25 | CAG CAAGG | CUAUUA | GAAACCUUAGGUU | AUAAA | GACCAAUGAUGCCUU | CCAGGU | CUUCU | >2 | 33 |
| B26 | CGUACC | GGCAAUC | GAAACCUUAGGUU | ACAUA | GACCAAUGAGCCGC | AC GGUCA | CUUCA | >2 | 34 |
| B27 | GAGACCA | GGCUGUU | GAAACCUUAGGUU | AAU | GACCAAUGAUGCCAU | GG GGCAUACUUCA | 0.38 | 35 |
| B28 | CUUC AAGG | CAGUGGU | GAAACCUUAGGUC | AAUA | UGACCAAUGAGCGCCGUCC | GGUU | CAACC | >2 | 36 |
| B30 | GAGACCC | GGCAGUGU | GAAACCUUAGGAU | ACAAA | AUCCAAUGAGGCCGA | CC CAUACUUCA | 0.17 | 37 |
| B31 | CU CUCGG | CUAUCU | GAAACCUUAGGAU | ACUUA | GACCAAUGAAGCCUU | CC GGUAACAUUC | 0.76 | 38 |
| B34 | AGUUCUU | GGCAGUCU | GAAACCUUAGGAU | ACUAA | AUCCAAUGAGGCCUU | CC GGUUA UAUCA | 1.6 | 39 |
| B35 | ACAUACCC | GGCGAUCG | GAAACCUUAGGUU | ACUAC | RACCCAAUGAGCGCCGU | CC GGACA | CAUAA | 0.54 | 40 |
| B41 | CUCC AAGCC | GCAAU | GAAACCUUAGGUU | AUAAA | RACCAAUGAGCCAC | CCAGGU A | CUUCA | >2 | 41 |
| B42 | UGUUCCU | GCAAUA | GAAACCUUAGGUU | ACUAC | GACCAAUGAGCCAU | CC GGCUA | CUUUG | 0.36 | 42 |
| B46 | CUCCU | GGCAGUGA | AAAACCUUAGGAA | OCGA | UUCCAAUGAAGCCAU | CC GGUUA | CUUCU | >2 | 43 |
| B53 | ACAA | GGCAAUUA | GAAACCUUAGGUUG | UUA | CAACCAAUGAUGCCAU | UC GGUCA | CUUCA | 1.5 | 44 |
| B55 | CUUCCGAGG | CAAUAGA | GAAACCUUAGGCU | AAAC | AACCAAUGAUGCCAU | CCAGG CAAG | UCA | 2.0 | 45 |
| B56 | AAAGCAA | GGCUAUCG | GAAACCUUAGGGU | GCAA | ACCCAAUGAGGCCUUU | CCGGG AA | CCUAA | 0.33 | 46 |
| B57 | CUUCCAAGG | CAAUAGA | AAACCUUAGGAU | ACAA | GUCCGAUGAAGCCAC | CC GGUCU | CGUCA | 0.43 | 47 |
|   |   |   |   |   |   |   |   | 0.98 | (47) |

| | 10 11 12 13 14 15 16 17 18 19 20 21 22 23 24 25 26 27 28 29 30 31 32 33 34 35 36 37 38 39 40 41 42 43 44 45 46 47 48 49 50 |
|---|---|
| A | 11 1 22 22 22 9 22 22 22 5 1 2 17 3 15 17 10 12 15 1 22 |
| G | 14 15 6 20 22 22 22 1 2 22 1 2 7 1 3 6 21 |
| C | 22 22 1 7 22 22 13 3 6 12 4 1 2 22 22 19 22 22 5 8 |
| U | 7 22 22 13 14 2 7 6 5 1 2 5 3 |

FIGURE 3A

5'-GGGAGCUCAGAAUAAACGCUCAA--[60N]--UUCGACAUGAGGCCCGGAUCCGGC-3'

CLASS 2

| Sequence Number | | Kd(μM)² | SEQ ID NO: |
|---|---|---|---|
| B11 | AAAACAGGACACCAUGAUAAAUGGACGAGUUCCUGGAGCGUCUAAAAGGGCACCCUUGA | >2  3.3 | 48 |
| B12 | UAACAGGACACCAUGAUUAAAUGGACGAGUUCCUACACUGGGCGGUUAAAAGAGCUCUCGAGGA | >2  ND | 49 |
| B17 | GAACAGGACACCAAGAGAUAAAUUGGACGAGUUCCUACUAGGGACGCUAUCGGCUGGCUCUCGAGGA | >2  2.4 | 50 |
| B29 | GAACAGGACACCUGGUUCUCAGGACGAGUUCCUACUAGGGACGCGCAAAAAGGGCUCUCGUGGG | >2  ND | 51 |
| B36 | AAACAGGACACCAAUUUUAUUGGACGAGUUCCUACUAGGGCGGUAUUAUGGGCUCGCGAGGA | >2  4.3 | 52 |
| B37 | AAACAGGACACCAUGAAA AUGAUUAUUGGACGAGUUCCUACUAGAGCGUUGCGCCCGUGGA | >2  4.7 | 53 |
| B48 | AAACAGGACACCAAGAUUAUUGGACGAGUUCCUACUAGGGCGAUUAAU GGGCUCGCGAUGA | >2  3.6 | 54 |
| B49 | AACAGGACACCUUGAAUAAAGGACGAGUUUACU GUGCGUUUAGUAGAACCCG GGA | >2  4.1 | 55 |

```
  3 4 5 6 7 8 9 10 11 12 13 14 15 16 17 18 19 20 21 22 23 24 25 26 27 28 29 30 31 32 33 34 35 36 37 38 39 40 41 42
A 8 8 8 8         6 3   1 7   6 2 3 6 4 2       2       8           8                 6 2   1       3
G     8 8 8 8                                           8   8   8 8       8 3 8       1 8 5 8 8   8 4
C   8                           8 8                                         5                 8       3
U                 2 4 1 2 6 4   1 3 6         8 8                 8 8 8         8 8     8
```

CLASS 3

| Sequence Number | | | | Kd(μM) 0.2 μMª | 1.0 μMᵇ | SEQ ID NO: |
|---|---|---|---|---|---|---|
| B23 | GCUCAAGG CAGAAACAGGACACACCA | AGACGAGUAACCA | GCCCAGCUUGACCAUACA | >2 | ND | 56 |
| B22 | AAGGUA AGAAACAGGACACGACACUUAAACAGAGUAACCAU | ACCUAGAUCGCGGAA | | >2 | 3.2 | 57 |
| B32 | AAAGGCACUGACCACCCUCAGGAAGAAUAA | CCGCGGUCACCCGCAUCCGAG | UCUAUCAAU | 0.26 | ND | 58 |

FIGURE 3B

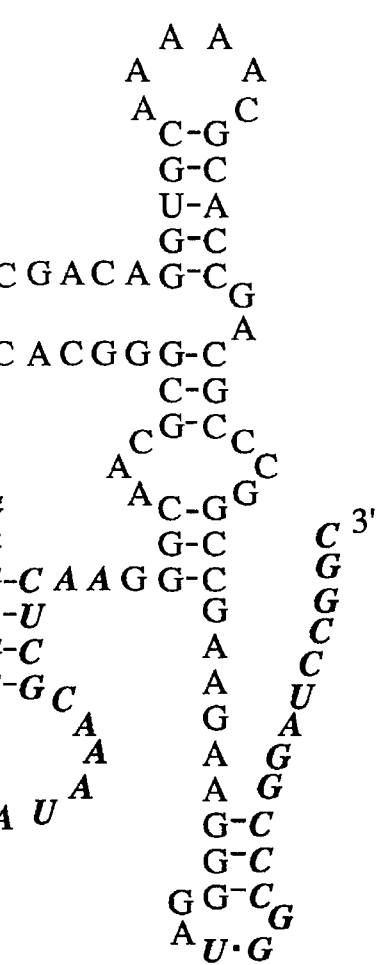
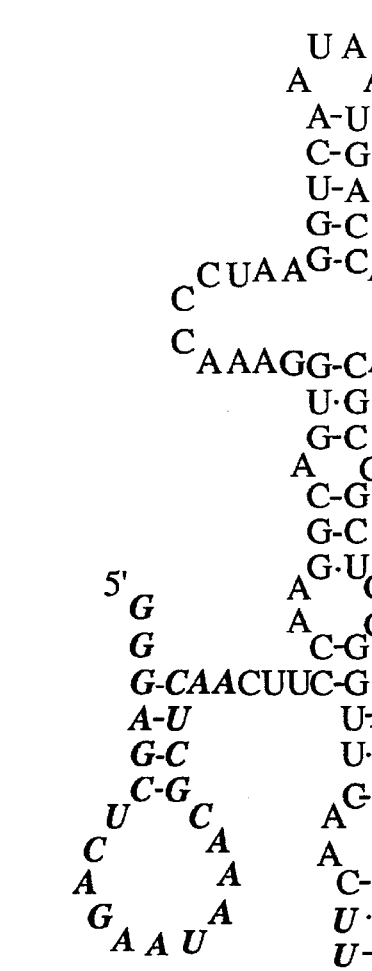
FIGURE 5A

Exp. B Class 1
Consensus

```
         W
      N     W
      R     V
       Y-D
       N-N
       G-C
   C U W A G-C R A
 C              U
 C              G
   A A A g N-N A
        U· g
        R···C
        W  c

5' ·· 3'
         ··
         ··
         ··
```

SEQ ID NO: 59

Exp. B Class 2
Consensus

```
           W
       W     H
      K       W
       D-H
       W-W
       C-G
      C-G
     A    A
      C-G   C
     A    A
      C-G   G
       A-U
       G·U
     A C A G-Y A
    A           C
     D A A C-G R
                 U
       U-D
       C-G
       G-C
       C-G
      5'    3'
        ··
        ··
        ··
```

SEQ ID NO: 60

SEQ ID NO: 66

FIGURE 5C 5,637,682

HIGH-AFFINITY OLIGONUCLEOTIDE LIGANDS TO THE TACHYKININ SUBSTANCE P

RELATED APPLICATIONS

This is a continuation of application(s) Ser. No. 08/303, 362 filed on Sep. 9, 1994.

This application is a Continuation-in-Part of U.S. patent application Ser. No. 07/714,131, filed Jun. 10, 1991, entitled Nucleic Acid Ligands, now issued as U.S. Pat. No. 5,475, 096, U.S. patent application Ser. No. 07/931,473, filed Aug. 17, 1992, entitled Nucleic Acid Ligands, now issued as U.S. Pat. No. 5,270,163, U.S. patent application Ser. No. 07/964, 624, filed Oct. 21, 1992, entitled Methods of Producing Nucleic Acid Ligands, now issued as U.S. Pat. No. 5,496, 938, and U.S. patent application Ser. No. 08/117,991, filed Sep. 8, 1993, entitled High-Affinity Nucleic Acid Ligands Containing Modified Nucleotides, now abandoned. U.S. patent application Ser. No. 07/714,131 is a Continuation-in Part of U.S. patent application Ser. No. 07/536,428, filed Jun. 11, 1990, entitled Systematic Evolution of Ligands by EXponential Enrichment, now abandoned.

This work was partially supported by grants from the United States Government funded through the National Institutes of Health. The U.S. Government may have certain rights in this invention.

FIELD OF THE INVENTION

Described herein are methods for identifying and preparing high-affinity nucleic acid ligands to the tachykinin substance P (SP). The method utilized herein for identifying such RNA nucleic acid ligands is called SELEX, an acronym for Systematic Evolution of Ligands by EXponential enrichment. Specifically disclosed herein are high-affinity RNA ligands.

BACKGROUND OF THE INVENTION

The peptide substance P (SP) is an eleven amino acid peptide (FIG. 1, SEQ ID NO:6) that belongs to the tachykinin family of neuropeptides. Known mammalian tachykinins (neurokinins) include neurokinin A, neurokinin B, neuropeptide K, and neuropeptide g. All tachykinins share the carboxy-terminal sequence Phe-Xaa-Gly-Leu-Met-$NH_2$ (where Xaa is an aromatic or aliphatic amino acid) (SEQ ID NO:61). The mammalian tachykinins are produced by neurons in the central and peripheral nervous system where they are predominantly localized in the nerve terminals (Escher, E. and Regoli, D. (1989) in *Peptide Hormones as Prohormones: Processing, Biological Activity, Pharmacology* (Martinez, J., ed.) pp 26–52, Ellis Horwood Limited, West Sussex, England).

Neurotransmitter and neuromodulator functions of SP include peripheral vasodilation, smooth muscle contraction, pain transmission (nociception), stimulation of exocrine secretions, and immunomodulation (for a review see Escher, E. and Regoli, D. (1989) in *Peptide Hormones as Prohormones: Processing, Biological Activity, Pharmacology*. (Martinez, J., ed.) pp 26–52, Ellis Horwood Limited, West Sussex, England). There is also evidence that SP has memory-modulating and reinforcing effects. Huston et al. (1993) Psychopharmacology 112: 147–162 have suggested a possible link between SP and the impairment in associative functioning accompanying Alzheimer's disease.

The pharmacological importance of substance P is further indicated by recent studies that suggest that SP has a role in angiogenesis (e.g., Fan, T. et al. (1993) *Brit. J. Pharmacol.* 110: 43–49). Fan et al. suggest that the positive interaction between SP and the cytokine interleukin-1 alpha (IL-1a) may be important in the angiogenic cascade leading to a variety of diseases characterized by excessive neovascularization (e.g., rheumatoid arthritis, atherosclerosis, diabetic retinopathy and cancer). Blocking substance P activity, therefore, may effectively reduce the progression of the disease.

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, now issued as U.S. Pat. No. 5,475,096, U.S. patent application Ser. No. 07/931,473, filed Aug. 17, 1992, entitled Nucleic Acid Ligands, now U.S. Pat. No. 5,270,163 (see also PCT/US91/04078), each of which is herein specifically incorporated by reference. Each of these applications, collectively referred to as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX." U.S. patent application Ser. No. 08/143, 564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, that describes oligonucleotides containing nuclgotide derivatives chemically modified at the 5- and 2'-positions of pyrimidines, as well as specific RNA ligands to thrombin containing 2'-amino modifications. U.S. patent Application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). Each of these applications is specifically incorporated herein by reference.

The development of high affinity ligands of SP are useful as diagnostic and pharmacological agents. Specifically, ligands capable of inhibiting SP would be useful in the treatment or monitoring treatment (i.e., diagnostic applications) of numerous diseases, including angiogenic diseases such as rheumatoid arthritis, atherosclerosis, diabetic retinopathy, and cancer. Herein described are high affinity nucleic acid ligands of SP. Considering the size of SP, it can be assumed that ligands of SP will be inhibitors of SP.

BRIEF SUMMARY OF THE INVENTION

The present invention includes methods of identifying and producing nucleic acid ligands to SP and the nucleic acid ligands so identified and produced. Specifically, RNA sequences are provided that are capable of binding specifically to SP. Included within the invention are the RNA ligand sequences shown in FIGS. 2 and 3.

Further included in this invention is a method for identifying nucleic acid ligands and nucleic acid ligand sequences to SP comprising the steps of (a) contacting a candidate mixture of single-stranded nucleic acids with SP, wherein nucleic acids having an increased affinity to SP relative to the candidate mixture may be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby nucleic acid ligands to SP may be identified.

Also included in this invention is a method of identifying nucleic acid ligands and nucleic acid ligand sequences to SP in solution comprising the steps of (a) preparing a candidate mixture of nucleic acids; (b) partitioning between members of said candidate mixture on the basis of affinity to immobilized SP; (c) amplifying the selected molecules to yield a mixture of nucleic acids enriched for nucleic acid sequences with a relatively higher affinity for binding to immobilized SP; (d) determining which of the nucleic acids from step (c) demonstrates binding to SP in solution; (e) selecting the nucleic acid ligand from the ligand mixture (d) that has the highest affinity for binding to SP in solution; (f) preparing a second candidate mixture of nucleic acids by mutagenizing the nucleic acid ligand selected in (e); and (g) repeating steps (b), (c), and (d). The mutagenesis allows the evolution of a more favorable primary sequence solution to higher order structures, since the initial experiment contained $10^{14}$ unique sequences, which is only a minute fraction of the $4^{60}$ possible sequences 60 nucleotides in length.

More specifically, the present invention includes the RNA ligands to SP identified according to the above-described method(s), including those ligands listed in FIGS. 2 and 3. Also included are RNA ligands to SP that are substantially homologous to any of the given ligands and that have substantially the same ability to bind SP. Further included in this invention are RNA ligands to SP that have substantially the same structural form as the ligands presented herein and that have substantially the same ability to bind SP.

The present invention also includes modified nucleotide sequences based on the RNA ligands identified herein and mixtures of the same.

BRIEF DESCRIPTION OF THE FIGURES

FIG. 1 shows the starting ssDNA template and RNAs, PCR primers, and peptides used in this study. For Cys-SP, "Ac" indicates that the peptide was synthesized with an acetylated N-terminus. (SEQ ID NOS:1–8).

FIG. 2 shows sequences from the 60N regions of RNA ligands selected in SELEX experiment A (SEQ ID NOS:5, 9–25). The full-length sequence includes the upstream and downstream fixed sequences as shown at the top of the Figure. Sequence numbers are preceded by the letter "A" to designate their selection in experiment A. The number of identical sequences among the 33 clones analyzed is indicated in parenthesis next to the sequence number. Groups 1–4 each represent a single "parental" sequence with variants resulting from point mutations presumably introduced by the polymerases used in the SELEX protocol. All unique sequences were placed in group 5. For sequences listed below the first sequences in groups 1–4, only differences from the first sequence are shown. Nucleotides listed below gaps in the first sequence indicate insertions. The hyphen in the ligand A14 sequence denotes the deletion of this nucleotide.

FIG. 3 shows alignments of sequences from the 60N (selected) regions of experiment B ligands (SEQ ID NOS:26–58). The full-length sequence includes the upstream and downstream fixed sequences as shown at the top of the Figure. The ligands have been assigned to three classes on the basis of sequence and secondary structure similarities. Secondary structure similarities were determined by phylogenetic comparison (Fox, G., and Woese, C. (1975) Nature 256: 505–507; Noller, H. F., and Woese, C. R. (1981) Science 212: 403–410). Sequence numbers are preceded by the letter B to designate their selection in experiment B. Nucleotide positions are numbered consecutively from a starting position dictated by aligned consensus sequences. Gaps in the sequences represent the absence of nucleotides at those numbered positions. $K_d$ measurements from single-point equilibrium dialysis binding experiments are shown to the right of the individual ligands. Binding reactions consisted of 20 nM $^3$H-SP ($P_o$) and either 0.2 µM RNA (a) or 1.0 µM RNA (b). ND=not determined. Nucleotide frequencies at the indicated positions are shown below the class 1 and 2 alignments.

FIG. 5A shows predicted secondary structures for ligands A13 (SEQ ID NO:5) and B28 (SEQ ID NO:36). The 23-nucleotide 5' and 25-nucleotide 3' fixed sequences complementary to the PCR primers are shown in bold italicized type. FIG. 5B shows consensus sequences and predicted secondary structures for the highly conserved regions of experiment B class 1 (SEQ ID NO:59) and 2 (SEQ ID NO:60) ligands. Universally conserved nucleotides are shown as normal capital letters. Lower case letters are used to indicate positions were a specific nucleotide is not universally conserved but occurs at a frequency of >90%. The following symbols are used to indicate other nucleotide patterns at individual locations: N=any base; R=A or G; Y=C or U; W=A or U; V=A , C, or G; K=G or U; D=A, G, or U; H=A, C, or U; . . .=base-pairing is sometimes, but not always, possible between these two nucleotide positions. In the class 2 consensus structure, the terminal seven nucleotides of the 5' fixed sequence are shown in bold italicized type. FIG. 5C depicts the secondary structure of SEQ ID NO:66.

DETAILED DESCRIPTION OF THE INVENTION

Figure 4:
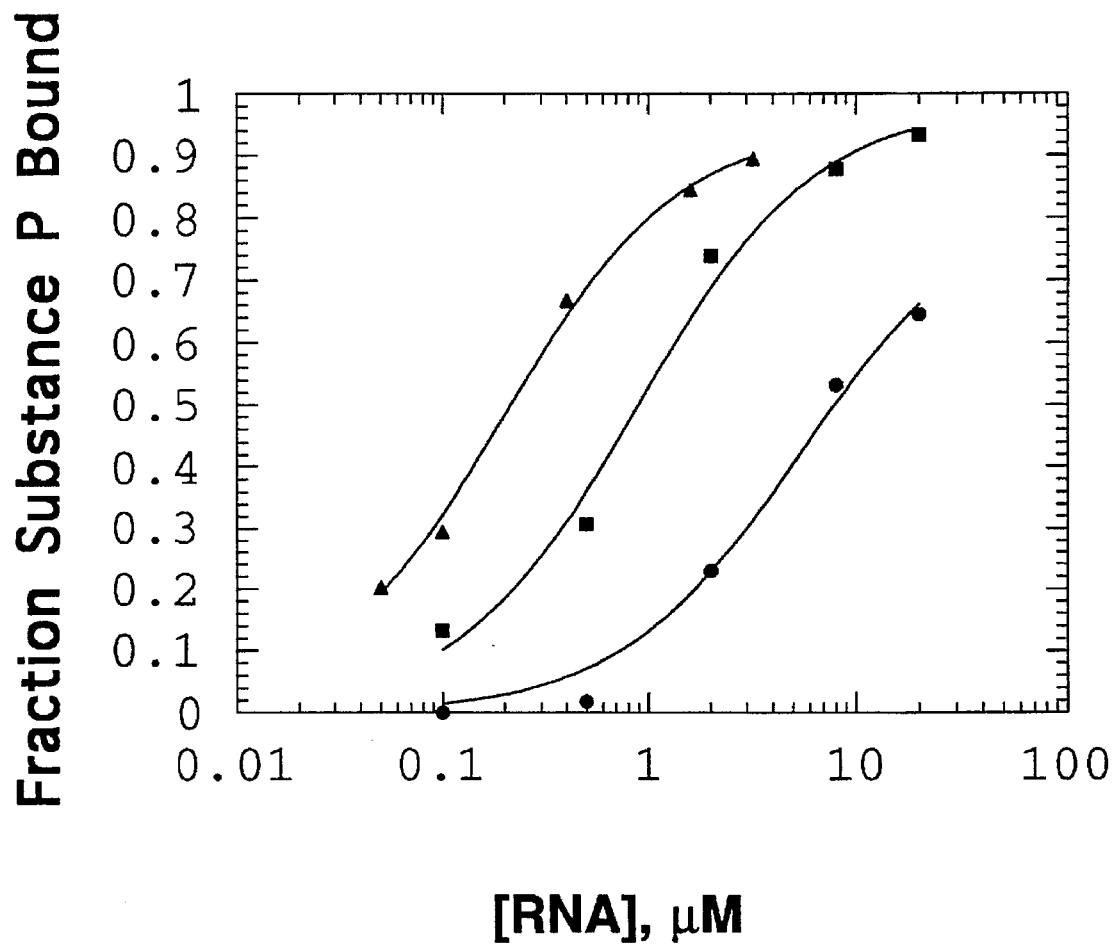
FIG. 4 shows binding curves for ligand A13 (SEQ ID NO:5) (△), experiment B selection cycle 12 pooled RNAs (■), and ligand B28 (SEQ ID NO:36) (●). The fraction of $^3$H-substance P bound in equilibrium dialysis experiments is plotted as a function of total RNA concentration. In each experiment, the concentration of substance P applied to one side of the dialysis membrane ($P_o$) was 20 nM. All binding reactions were at room temperature in 1X substance P binding buffer.

This application describes high-affinity oligonucleotide ligands to SP identified through the method known as SELEX. The SELEX method is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now issued as U.S. Pat. No. 5,475,096, U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below; (b) to mimic a sequence known to bind to the target; or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 1–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligand solutions obtained to a number of target species, including both protein targets where the protein is and is not a nucleic acid binding protein.

SELEX provides high affinity ligands to a target molecule. This represents a singular achievement that is unprecedented in the field of nucleic acids research. The present invention applies the SELEX procedure to the specific target of SP. In the Example section below, the experimental parameters used to isolate and identify the nucleic acid ligands to SP are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 now issued as U.S. Pat. No. 5,496,938 ('938), methods are described for obtaining improved nucleic acid ligands after SELEX has been performed. The '938 patent, entitled Methods of Producing Nucleic Acid Ligands, is specifically incorporated herein by reference. In the present invention, a SELEX experiment was performed in search of a nucleic acid ligand with specific high affinity for SP from a degenerate library containing 60 random positions (60N).

A systematic evolution of ligands by exponential enrichment (SELEX) procedure was used to isolate RNAs that bind substance P immobilized on a solid support (Example 2). RNAs that also bind substance P in solution were identified and the tightest binder was subjected to mutagenesis in a second SELEX procedure to evolve ligands with a higher affinity for the peptide (Example 3). A comparative analysis of 36 ligands isolated from the second SELEX experiment revealed two main sequence classes with highly conserved secondary structures within each class (Example 4). Dissociation constants for the interaction of these ligands with SP in solution were determined by equilibrium dialysis. The amino acid residues involved in the interaction with the highest affinity ligand (190 nM $K_d$) were mapped by determining which of a set of overlapping fragments of substance P can compete with the intact peptide for binding (Example 5). A binding competition experiment also demonstrated the ability of the same ligand to discriminate between substance P and the reverse orientation of the same amino acid sequence (Example 6). The results from this study demonstrate that SELEX can yield high affinity RNA ligands to small non-constrained peptides.

This invention includes the specific RNA ligands to SP shown in FIGS. 2 and 3 (SEQ ID NOS:5,9–58), identified by the method described in Examples 1–3. The scope of the ligands covered by this invention extends to all nucleic acid ligands of SP, modified and unmodified, identified according to the SELEX procedure. More specifically, this invention includes nucleic acid sequences that are substantially homologous to the RNA ligands shown in FIGS. 2 and 3. By substantially homologous it is meant a degree of primary sequence homology in excess of 70%, most preferably in excess of 80%. A review of the sequence homologies of the RNA ligands of SP shown in FIG. 2 and 3 shows that sequences with little or no primary sequence homology may have substantially the same ability to bind SP. For these reasons, this invention also includes nucleic acid ligands that have substantially the same ability to bind SP as the nucleic acid ligands shown in FIGS. 2 and 3. Substantially the same ability to bind SP means that the affinity is within one to two orders of magnitude of the affinity of the ligands described herein. It is well within the skill of those of ordinary skill in the art to determine whether a given sequence—substantially homologous to those specifically described herein—has substantially the same ability to bind SP.

This invention also includes the ligands as described above, wherein certain chemical modifications are made in order to increase the in vivo stability of the ligand or to enhance or mediate the delivery of the ligand. Examples of such modifications include chemical substitutions at the ribose and/or phosphate and/or base positions of a given nucleic acid sequence. See, e.g., Cook et al. PCT Application WO 92/03568; U.S. Pat. No. 5,118,672 of Schinazi et al.; Hobbs et al. (1973) Blochem. 12: 5138; Guschlbauer et al. (1977) Nucleic Acids Res. 4: 1933; Shibahara et al.; (1989) Nucleic Acids Res. 15: 4403; Pieken et al. (1991) Science 253: 314. Such modifications may be made post-SELEX (modification of previously identified unmodified ligands) or by incorporation into the SELEX process.

Additionally, the ligands can be modified by mutagenesis either during the SELEX process or post-SELEX to yield ligands with better properties. PCR mutagenesis is described in detail below, however, any mutagenesis process known to one of ordinary skill in the art can be applied in a similar manner.

The following examples are provided to explain and illustrate the present invention and are not to be taken as limiting of the invention.

EXAMPLE 1

EXPERIMENTAL PROCEDURES

This Example will provide general procedures followed and incorporated into the specific Examples that follow.

Materials. Synthetic single-stranded DNAs (ssDNA) were obtained from Operon (Alameda, Calif.). Cys-SP (SEQ ID NO:7) and Cys-rSP (SEQ ID NO:8) were synthesized and purified by Macromolecular Resources (Fort Collins, Colo.). Thiopropyl-activated Sepharose 6B, SP, and all SP fragments with the exception of SP 1–6 were purchased from Sigma. SP 1–6 was purchased from Peninsula Laboratories, Inc. (Belmont, Calif.). [2-L-Prolyl-3,4-$^3$H(N)]-SP and all radionucleotides were obtained from NEN Research Products (Dupont; Wilmington, Del.). Enzymes were purchased from commercial sources.

Immobilizing SP on thiopropyl-activated Sepharose. Cys-SP (FIG. 1, SEQ ID NO:7) was covalently coupled (disulfide bond) to thiopropyl-activated Sepharose 6B through an interaction of the Cys-thiol group of peptides with hydroxypropyl-2-pyridyl disulfide ligands of the matrix. The coupling reaction consisted of 1.4 mg Cys-SP and 1 g pre-swollen thiopropyl-Sepharose in a final volume of 7 ml in the following buffer: 500 mMNaCl, 1 mM EDTA, 10 mM Tris-Cl, pH 8.4. The suspension was gently mixed for 1 hr at 4° C., then transferred to a chromatography column and washed with 30 ml of 100 mM sodium acetate, pH 6.0. Remaining hydroxypropyl-2-pyridyl disulfide ligands were reacted by suspending the matrix in 7 ml of 100 mM sodium acetate plus 5 mM β-mercaptoethanol, followed by gentle mixing at room temperature for 45 min. The matrix was washed in SP binding buffer (10 mM HEPES, pH 7.0, 150 mMNaCl, 5 mM KCl, 5 mM $CaCl_2$), and the concentration of bound peptides was quantitated by ninhydrin assays. Storage was in SP binding buffer with 0.1% sodium azide at 4° C. Thiopropyl Sepharose 6B utilized for counterselection and the dilution of SP-Sepharose was prepared as described above except for the omission of SP.

Random sequence RNA pool. Template DNA for the initial random sequence RNA population was generated from a synthetic random sequence ssDNA pool (FIG. 1, SEQ ID NO:4). The random region was generated by utilizing a mixture of the four unmodified nucleotides (the molar ratios of which are adjusted to yield a 1:1:1:1 ratio of incorporated nucleotides) during oligonucleotide synthesis. The ssDNAs contained 60 nucleotides of contiguous random sequence flanked by defined 5' and 3' ends that permit primer hybridization (FIG. 1). Double-stranded DNA (dsDNA) molecules, synthesized initially by klenow enzyme, and subsequently (following cycles of selection) by Taq DNA polymerase, have a T7 RNA polymerase promoter at the 5' end. In vitro transcription of 500 pmoles (~$3\times10^{14}$ unique sequences) of dsDNA template yielded the initial pool of uniformly [a-$^{32}$P]GTP-labeled 107-nt random sequence RNAs.

SELEX Experiment A. This experiment identifies RNA ligands which bind to SP. Uniformly $^{32}$P-labeled RNAs were suspended in 25 μl of SP binding buffer, heated at 70° C. for 5 min, then cooled to room temperature. The quantity of RNA used for each selection cycle is indicated in Table 1. The RNA suspension was applied to a 100-μl SP-Sepharose column (80 μM SP) at room temperature, followed by 10 200-μl SP binding buffer wash volumes. Peptide-bound RNAs were then recovered with five 200-μl volumes of binding buffer containing 100 mM dithiothreitol (DTT). DTT reduces the linker disulfide bond resulting in the release of peptide from the matrix. The DTT eluate was extracted once with phenol and the RNAs were recovered by ethanol precipitation with 20 μg of yeast tRNA as carrier. Reverse transcription, PCR amplification, and T7 RNA polymerase transcription were performed essentially as described in (Tuerk, C. and Gold, L. (1990) Science 249: 505–510). Transcription of PCR products yielded the RNA pool for the next cycle of selection and amplification.

Prior to some of the selection cycles, a counterselection procedure was done as indicated in Table 1. The counterselection process entailed applying the RNA suspension to a thiopropyl-Sepharose column (not coupled with SP) and unbound RNA was then applied to the SP-Sepharose column as described above.

SELEX Experiment B. This experiment was performed in an attempt to find ligands with a higher affinity to SP by mutagenizing the highest affinity ligand identified in Experiment A. Random mutagenesis (by the PCR mutagenesis procedure described below) of the highest affinity ligand from Experiment A (ligand A13 (SEQ ID NO:5) described in Example 2 below) provided the template DNA used to initiate Experiment B. Uniformly $^{32}$P-labeled RNAs (200 pmoles for each selection cycle) were suspended in 400 μl of 188 mM NaCl, denatured by heating at 90° C. for 90 sec, then quick-cooled on ice. After the addition of 100 μl 5X SP binding buffer (minus NaCl), the RNA was combined with a 100-μl column volume of SP-Sepharose suspended in 400 μl SP binding buffer. SP concentrations (as a function of column volume) used for each selection cycle are listed in Table 2. The 1 ml suspension was mixed on a rocking plateform at room temperature for 30 min. An identical binding procedure was followed for cycles in which a counterselection column (no peptide) preceded the SP-Sepharose column in the selection scheme (indicated in Table 2). Bound RNAs were pelleted with the counterselection matrix by centrifugation (~1000 x g, 5 sec) and a 100-μl column volume of SP-Sepharose was suspended in the supernatant. Following the 30 min incubation, the SP-Sepharose was pelleted as above, and the supernatant was removed. The matrix was resuspended in 400 μl binding buffer and transferred to a syringe column (shortened 1-ml syringe with a small quantity of glass wool at the bottom). The flow-through volume was collected and the column was washed with an additional 10 200-μl volumes of binding buffer. Peptide-bound RNAs were eluted with five 200-μl volumes of binding buffer containing 100 mM DTT. RNAs were recovered as in Experiment A and amplified. PCR amplification following selection cycles 1–5 was by the PCR mutagenesis procedure described below. Standard PCR amplification followed selection cycles 6–12.

PCR mutacenesis. Essential features of a modified PCR procedure for the introduction of random point mutations into DNA are well-known in the art and are described in (Cadwell, R. C., and Joyce, G. F. (1992) PCR Methods Appl. 2: 28–33; Barrel, D. P., and Szostak, J. W. (1993) Science 261: 1411–1418; and Leung, D. W. et al. (1989) Technique 1: 11–15). In Experiment B of this study, the reaction mixture for selection cycle one consisted of 5 pmoles ligand A13 (SEQ ID NO:5) dsDNA (for selection cycles 2–6, all of the cDNA recovered from the prior selection cycle served as template), 1 mM dCTP, 1 mM dTTP, 0.2 mM dGTP, 0.2 mM dATP, 7 mM MgCl$_2$, 0.55 mM MnCl$_2$, 100 pmoles of each primer, and 3 units of Taq polymerase (Promega) in 100 μl Taq buffer (supplied with enzyme). The mixture was subjected to three PCR cycles: each cycle was 93° C., 45 sec; 50° C., 45 sec; and 72° C., 2 min. A 13 μl volume of the reaction was transferred to a new tube and brought up to 100 μl with fresh reaction buffer (same composition minus template) followed by an additional three cycles of PCR mutagenesis. This dilution-PCR mutagenesis procedure was repeated nine more times for a total of 11 3-cycle reactions (33 doublings). Products from the 11th 3-cycle reaction were amplified further by diluting 13 μl of the reaction in 87 μl of a standard PCR reaction mixture (0.4 mM dNTPs, 3.75 mM MgCl$_2$, 250 pmoles of each primer, and 5 units of Taq polymerase in 1X Taq buffer) followed by 8 PCR cycles. Products from the final reaction were used as template for T7 RNA polymerase transcription. To analyze the mutation results, PCR products from the final amplification of PCR-mutagenized ligand A13 (for selection cycle 1) were cloned and sequenced.

DNA sequencing. PCR products were cloned into the Hind III and BamHI restriction sites of pUC18 and sequenced by the dideoxynucleotide termination method using modified T7 DNA polymerase (Sequenase 2.0; United States Biochemical) and universal forward and reverse primers.

Figure 6:
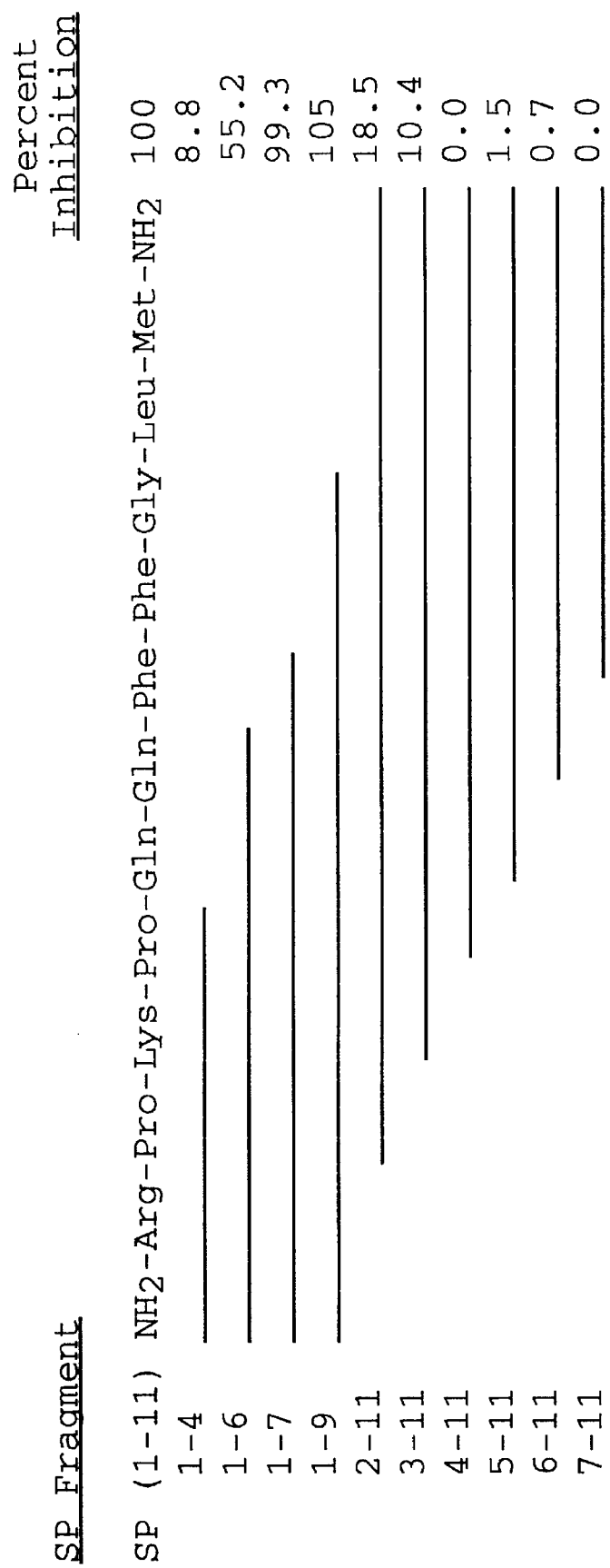
FIG. 6 shows competition between substance P fragments and intact substance P for binding to ligand B28 (SEQ ID NO:36). Equilibrium dialysis binding reactions consisted of 1.6 µM ligand B28 RNA, 1.6 µM substance P ($P_o$; including 20 nM $^3$H-substance P), and 32 µM (20-fold excess) of the competing peptide fragment. The fraction of $^3$H-substance P bound in the absence of added competitor was 0.63. An 86.1% decrease (inhibition) in $^3$H-substance P bound was observed in the presence of 32 µM ($P_o$) competing unlabeled substance P. The percent decrease (inhibition) in $^3$H-substance P bound in the presence of individual substance P fragments is expressed relative to intact substance P=100% inhibition.

Equilibrium dialysis. Equilibrium dialysis experiments were performed with a Spectra/Por® (Spectrum; Houston, Tex.) equilibrium dialyzer, Spectra/Por® (Spectrum; Houston, Tex.) microcell dialysis chambers (200-μl chamber volumes), and 12000–14000 MWCO dialysis membranes (Spectrum; Houston, Tex.). These membranes allow passage of SP but not 107-nt RNAs. Sample volumes were 200 μl on each side of the membrane (i.e., 200 μl per chamber). All experiments were at room temperature in 1X SP binding buffer. RNAs (unlabeled) were denatured prior to re-equilibration in binding buffer as described above for Experiment B. For binding curves (FIG. 4), RNA concentrations between 50 nM and 20 μM were utilized. Single point $K_d$ estimates for individual Experiment B ligands were performed with 200 nM or 1 μM RNA. The concentration of $^3$H-SP applied to one side of the membrane ($P_o$; this symbol is used throughout this application to denote the peptide concentration as applied to one side of the membrane) was 20 nM for binding curves and single-point $K_d$ estimates. For binding competition experiments (FIGS. 6 and 7), equal concentrations of the competing peptide were applied to each side of the membrane at the start of dialysis. The dialysis cells were rotated at 10 rpm to shorten the time required to reach equilibrium. Equilibrium dialysis initiated with $^3$H-SP on one side of the membrane and in the absence of RNA was performed to determine the length of time required to attain equilibrium (~2.5 hours for Spectra/Por®-2 membranes); dialysis times for binding measurements were at least one hour longer than this determined time. Following equilibration, samples were withdrawn from the dialysis chambers, added to scintillation fluid, and counted.

Determining Equilibrium Dissociation Constants. Equilibrium dissociation constants ($K_d$) were defined by the following equation (Rosen, D. et al. (1980) Biochemistry 19: 5687–5692):

$$K_d = [R_f][P_f]/[P_b]$$

where $R_f$ is the concentration of unbound RNA (i.e., total RNA minus $[P_b]$), $P_f$ is the concentration of unbound peptide (concentration on the side of the membrane that does not contain RNA), and $[P_b]$ is the concentration of peptide bound to RNA ([P] on side of membrane that contains RNA minus $[P_f]$). Donnan effects were neglected in $K_d$ measurements because it was assumed that this problem would be overcome by the high NaCl concentration (Karush, F. and Sonnenberg, M. (1949) J. Amer. Chem. Society 71: 1369). The fraction of SP bound was calculated by dividing $[P_b]$ by $[P_t]$, where $[P_t]$ is the total peptide concentration in the dialysis chamber containing RNA.

EXAMPLE 2

RNA LIGANDS TO SP

Ligands generated by Experiment A. RNA ligands with affinity for SP were isolated in SELEX Experiment A described in Example 1 by selecting for RNAs present in a random sequence pool that bind SP immobilized on a solid support. The initial random sequence RNA population for experiment A consisted of approximately $3 \times 10^{14}$ unique molecules, each with 60 nt of contiguous random sequence (SEQ ID NO:4). RNA 5' and 3' defined ends and their complimentary primer sequences are shown in FIG. 1. The dissociation constant of the unselected random sequence RNA pool was roughly estimated at 1.2 mM as indicated by an equilibrium dialysis experiment (see Example 1, supra) with 20 µM RNA and 20 nM ($P_o$) of $^3$H-SP where the fraction of SP bound was 0.017. The constraints of the dialysis system prohibited the use of significantly higher concentrations of RNA in the analysis. For the first selection cycle, 500 pmoles of RNA was used; this quantity was reduced as the copy number of individual species increased (200 pmoles in cycle 2 and 50 pmoles for the remaining cycles). RNA pools subjected to selection cycles 5–12 were first counterselected on thiopropyl-Sepharose 6B (see Example 1) to remove RNAs with affinity for Sepharose or the linker arm. A significant increase in binding to SP was observed after the seventh selection cycle, with only a moderate improvement in subsequent cycles (Table 1). AMV reverse transcriptase sequencing of RNA pools showed a significant decrease in sequence randomness following selection cycles 7–12 (data not shown). No additional change in the sequence pattern was observed for RNA pools generated from selection cycles 10–12, suggesting that no further enrichment was occurring under these conditions.

PCR products from the 12th cycle of selection and amplification were cloned and sequenced as described in Example 1. Of the 33 clones sequenced, 18 are unique (FIG. 2) (SEQ ID NOS:5, 9–25). However, 10 of the unique sequences may have resulted from point mutations within a selected sequence during the amplification or cloning procedures (see sequence groups 1–4, FIG. 2). Representatives of each sequence group were analyzed by equilibrium dialysis for their ability to bind SP in solution. Only group 3 and group 4 ligands (SEQ ID NOS:5, 18–21) demonstrated binding to free SP at RNA and peptide concentrations of 4 µM and 2 µM ($P_o$), respectively. Ligand A13 (SEQ ID NO:5), with an estimated $K_d$ of 14 µM under these conditions, exhibited the highest affinity for SP in solution. The $K_d$ for ligand A13 was subsequently more accurately estimated at 5.8 µM with a five-point binding curve (FIG. 4), an improvement in affinity of about 200-fold over the initial unselected random sequence RNA pool. Sequence groups which did not exhibit binding to free SP under these conditions were presumably selected for their affinity to an SP conformation that is more prevalent when the peptide is coupled to the matrix, or to an epitope that includes portions of both the peptide and the linker arm. Alternatively, ligands with affinity for the linker arm alone may have escaped the counterselection process resulting in their subsequent elution with DTT.

EXAMPLE 3

SELECTING FOR HIGHER AFFINITY LIGANDS TO SP BY MUTAGENESIS

Ligands Generated by Experiment B. Higher affinity ligands to SP were produced and isolated in Experiment B described in Example 1. Using ligand A13 dsDNA (SEQ ID NO:5) as described in Example 2 as the starting template source, an additional 12 cycles of selection and amplification were performed with PCR mutagenesis preceding the first six selection cycles. It was assumed that mutagenesis of ligand A13 would yield ligands with a higher affinity for SP because the random sequence pool used to initiate Experiment A contained about $10^{14}$ unique sequences, only a minute fraction of the $4^{60}$ possible sequences 60 nucleotides in length. Under these conditions, the evolution of a more favorable primary sequence solution to higher ordered structures would be essentially unavoidable. PCR products from the initial mutagenic PCR amplification of ligand A13 (RNA produced from this template pool was used for the first selection cycle) were cloned and sequenced to investigate the mutagenesis procedure. Ninety-six point mutations were identified within the 60N regions of 25 clones sequenced, representing a mutation rate of 0.064 per nucleotide position. At this rate, an average of 3.8 point mutations was expected per RNA per each of the first six selection cycles. Transition and transversion frequencies were equal (48 of each), and the mutations appeared to be randomly distributed throughout the sequence space. However, as observed by Barrel and Szostak (Barrel, D. P., and Szostak, J. W. (1993) Science 261: 1411–1418), there was a bias in the types of mutations induced. With the non-mutated 60N region of clone A13 having a nucleotide representation of 22 G, 20 C, 17 A, and 1 U, the following point mutations were identified: A•T to T•A (30), A•T to G•C (22), C•G to T•A (14), G•C to A•T (10), C•G to A•T (8), G•C to T•A (4), G•C to C•G (2), A•T to C•G (2), T•A to C•G (2), T•A to A•T (2), T•A to G•C (0), and C•G to G•C (0).

Selective pressure for the tightest binders was also increased in Experiment B by reducing the peptide concentration following cycles in which binding had significantly increased (Table 2). The matrix-coupled SP concentrations were effectively lower than those listed in Table 2 (given as a function of column volume; 100 µl), since binding occurred in a well-mixed 1-ml suspension. For selection cycles 8–12, a counterselection thiopropyl Sepharose matrix was used prior to SP affinity selection. An RNA pool generated from cycle 12 PCR products exhibited a dissociation constant of 0.80 µM for SP in an equilibrium dialysis binding experiment (FIG. 4), a 7-fold improvement in binding over ligand A13. PCR products from the 12th selection cycle were cloned and sequenced. Of the 33 clones sequenced, all were unique (SEQ ID NOS:26–55). However, all but three of the sequences can clearly be placed into two major sequence classes (FIG. 3).

Binding of Ligands to SP in Solution. All 33 mutagenized clones were screened for their ability to bind SP in solution by single-point equilibrium dialysis measurements (FIG. 3).

Ligands assigned to class 1 generally have the highest affinity for SP in solution, with ligand B28 (SEQ ID NO:36) having the lowest $K_d$ (measured at 170 nM in this screen). A five-point binding curve was subsequently performed by equilibrium dialysis (see Example 1) to obtain the more reliable ligand B28 $K_d$ measurement of 190 nM (FIG. 4). Experiment B, therefore, yielded ligands with binding affinities up to 30-fold better than their ancestral ligand A13 and approximately 6,000-fold better than the initial unselected random sequence RNA pool. With the exception of class 3 ligand B32 (SEQ ID NO:58), all class 2 and class 3 ligands exhibited a $K_d$ above 2 µM (FIG. 3). A comparison of nucleotide positions 4–22 of the high affinity class 3 ligand B32 (SEQ ID NO:58) with positions 10–28 of class 1 ligands reveals a significant sequence similarity (GGC$_7$ACCCUNAGG) (SEQ ID NO:62), indicating the probable importance of this region in SP binding. The lower affinity class 3 ligands (B22 and B23) (SEQ ID NOS:57 and 56, respectively) share significant stretches of sequence homology with the relatively low affinity class 2 ligands: ACAGGACAC and GACGAGUU at positions 4–12 and 24–31 in the class 1 alignment, respectively (FIG. 3).

EXAMPLE 4

Predicted Secondary Structure of Selected Ligands. A comparative analysis of sequences within class 1 and 2 of FIG. 3, with base-pairing decisions influenced by observed covariation, led to the prediction of possible secondary structures (FIG. 5). This approach, known as the phylogenetic comparative approach, is a reliable method for determining secondary and tertiary structures of RNAs (and ssDNAs) (Fox, G. and Woese, C. (1975) Nature 256: 505–507; Noller, H. F., and Woese, C. R. (1981) Science 212: 403–410). With this approach, one looks for structural features that are conserved despite differences in the primary sequence of the nucleic acids (i.e., covariance). As an example, if an equivalent base-pairing scheme in a putative RNA helical region is not present in homologous regions of phylogenetically and functionally related RNAs, it is unlikely that it exists in the RNA's functional structure. Despite the high degree of sequence variability introduced during experiment B, a consensus structure predicted for the class 1 ligands resembles that predicted for A13 (SEQ ID NO:5) (FIG. 5). The large number of selected mutations is not completely unexpected, as the random sequence RNA pool used to initiate experiment A contained about $10^{14}$ unique sequences, only a minute fraction of the $4^{60}$ possible sequences 60 nucleotides in length. Under these conditions, the evolution of a more favorable primary sequence solution to higher ordered structures would be essentially unavoidable. Conserved nucleotides within the large asymmetric loop present in both the predicted ligand A13 (SEQ ID NO:5) structure and the class 1 consensus structure suggest a role for these nucleotides in binding. The majority of the nucleotides within this loop are completely conserved among class 1 ligands. In addition, the sequence within the high affinity class 3 ligand (B32) (SEQ ID NO:58) that is shared with the class 1 ligands (ACCCUNAGG) is present within this loop. Experiment B class 2 ligands share a high degree of primary and secondary structure similarity; all can assume a stem-loop structure with two internal asymmetric loops (FIG. 5). Most of the internal loop nucleotides are conserved, suggesting their involvement in the SP interaction. The nucleotides conserved among the lower affinity class 3 ligands (B22 and B23) (SEQ ID NOS:57 and 56, respectively) and the class 2 ligands (listed above) are partially present in the two internal loops and form the stem that separates them.

EXAMPLE 5

Amino Acids Required for Interaction with Ligand B28. To determine which amino acids are required for the interaction with ligand B28 (SEQ ID NO:36), overlapping fragments of the peptide were tested for their ability to compete with intact SP (SEQ ID NO:6) for binding in equilibrium dialysis experiments, as described above. Each competition experiment contained 1.6 µM B28 RNA and 1.6 µM SP ($P_o$; including 20 nM $^3$H-SP), in addition to 32 µM ($P_o$) of the competing peptide fragment (20:1 ratio of competing peptide to SP). In the absence of competing peptide, 63% of the SP was bound under these conditions. The percent inhibition observed with 32 µM competing unlabeled SP (as a positive control) was 86%. The results (FIG. 6) indicate that the four C-terminal residues (Phe$^8$-Gly$^9$-Leu$^{10}$-Met$^{11}$-NH$_2$) (SEQ ID NO:63) are not necessary for binding. The presence of Phe$^7$ appears to be required for optimal binding, but is not entirely necessary. The involvement of Arg$^1$ in the interaction is indicated by the inability of fragment 2–11 to compete under these conditions. However, the four N-terminal residues (Arg$^1$-Pro$^2$-Lys$^3$-Pro$^4$) (SEQ ID NO:64) alone did not exhibit significant binding, suggesting a requirement for one or both of the Gln residues. Taken together, the results suggest that, minimally, Arg$^1$ and Gln$^5$-Gln$^6$-Phe$^7$ are involved in the interaction with ligand B28 (SEQ ID NO:36).

EXAMPLE 6

Figure 7:
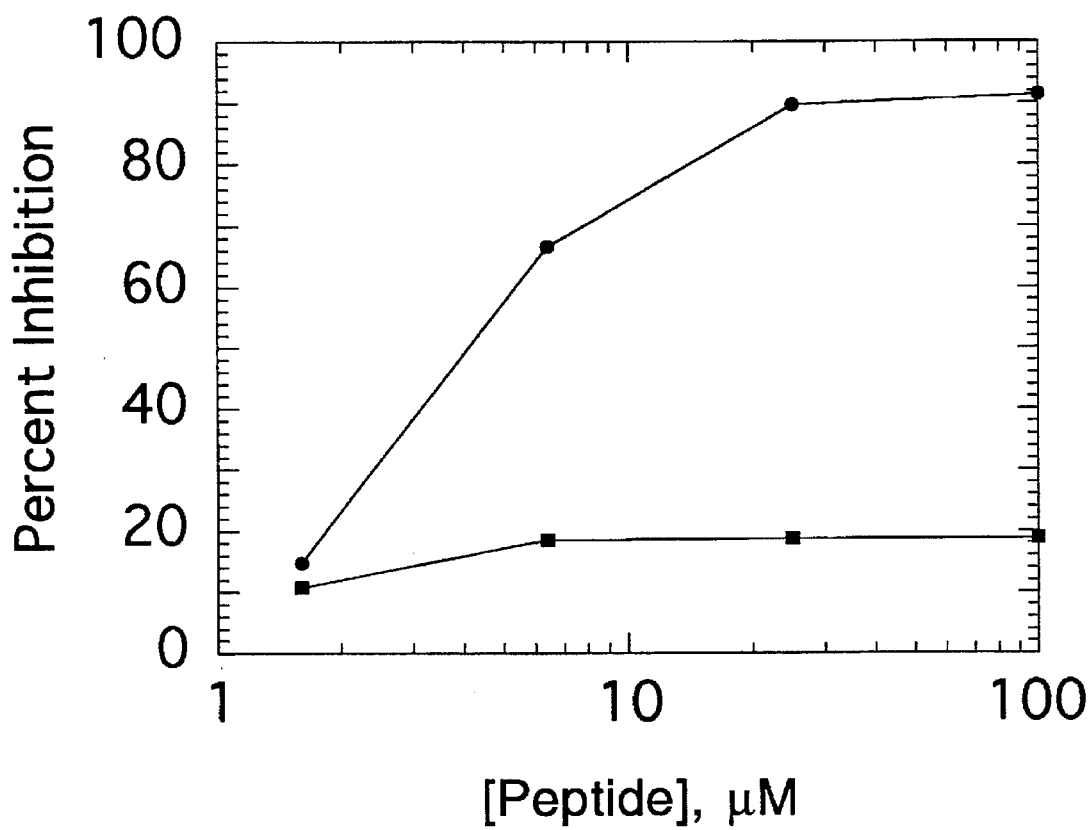
FIG. 7 shows a plot of percent inhibition of $^3$H-substance P bound to ligand B28 (SEQ ID NO:36) in the presence of varying concentrations of unlabeled substance P (SEQ ID NO:6) (■) or a peptide (rSP) which contains the same amino acid sequence as substance P but in the reverse orientation (SEQ ID NO:8) (■). Each equilibrium dialysis binding reaction consisted of 1.6 µM ligand B28 RNA and 1.6 µM of substance P ($P_o$; including 20 nM $^3$H-substance P) in addition to the competing peptide at a concentration of 0, 1.6, 6.4, 25, or 100 µM. The percent decrease (inhibition) in the fraction of $^3$H-substance P bound in the presence of competing peptide is expressed relative to the fraction of $^3$H-substance P bound in the absence of added competitor (0.69).

Specificity of ligand B28 for SP over rSP. A high specificity of ligand B28 (SEQ ID NO:36) for SP was suggested by the ability of the ligand to discriminate between SP and the reverse orientation of the same peptide (rSP, FIG. 1). An equilibrium dialysis competition experiment was performed as above, except the competing concentrations ($P_o$) of rSP were either 1.6, 6.4, 25, or 100 µM. Competition experiments with unlabeled SP at the same concentrations were performed for comparison. In the absence of added competitor, 69% binding of SP was observed under these conditions. The data indicate that rSP is a poor competitor for binding to ligand B28 (SEQ ID NO:36) (FIG. 7). Knowing that multiple amino acid residues are involved in the interaction (FIG. 6), it can be assumed that SP possesses a unique structure, with unique relative positions of amino acid side chains, as it is recognized by the ligand. Although this recognized structure might include the N-terminal arginine alpha-amine of free SP, the N-terminus of the column-coupled peptide (Cys-SP, FIG. 1), to which ligands were selected, was acetylated. Chassaing et al. (1986) Eur. J. Biochem. 154: 77–85 have proposed a preferred conformation of SP in methanol consisting of a flexible Arg$^1$-Pro$^2$-Lys$^3$ N-terminus, and alpha-helical structure involving residues Pro$^4$-Gln$^5$-Gln$^6$-Phe7-Phe$^8$ (SEQ ID NO:65) and an interaction of the C-terminal carboxamide with the primary amides from both glutamines. An alpha-helical structure may not exist in the core residues of rSP, for instance, because these residues would not have the benefit of the helix-nucleating properties of proline (Presta, L. G., and Rose, G. D. (1988) Science 240: 1632–1641).

EXAMPLE 7

Modified 2'-NH$_2$ Pyrimidine RNA Ligands to SP. In order to generate ligands with improved stability in vivo, an experiment is carried out with randomized RNA containing amino (NTH$_2$) functionalities at the 2'-position of each pyrimidine. A library of $10^{14}$ RNA molecules is generated that contains 60 nucleotides of contiguous random sequence flanked by defined sequences. Defined nucleotide sequences in the flanking regions of the template serve as primer annealing sites for PCR and also provide the promoter sequence (e.g., T7) required for transcription. The random nucleotides of the initial candidate mixture are comprised of 2'-$NH_2$ pyrimidine nucleosides. The rounds of selection, amplification, and optionally mutagenesis are carried out as described in Examples 1–3 using art-known techniques.

To avoid the selection and amplification of undesired RNA molecules that bind to matrix components other than the target peptide, counterselection steps preceding the selection steps are incorporated into the selection process (as described above). These steps are reiterated until the enriched pool of RNA shows significantly improved affinity to SP over the initial random pool. The resulting RNA ligands are reverse transcribed and the cDNAs are PCR amplified. The dsDNA PCR products are cloned into a plasmid vector and sequenced as described above.

TABLE 1

Summary of SELEX experiment A selection cycle results.
Experiment A

| Selection cycle | pmoles RNA [a] | Counterselection column ? [b] | Percent eluted with DTT [c] |
| --- | --- | --- | --- |
| 1 [d] | 500 | N | 0.47 |
| 1 | 500 | N | 0.35 |
| 2 | 200 | N | 1.92 |
| 3 | 50 | N | 0.77 |
| 4 | 50 | N | 0.61 |
| 5 | 50 | Y | 2.57 |
| 6 | 50 | Y | 1.52 |
| 7 | 50 | Y | 2.27 |
| 8 | 50 | Y | 13.8 |
| 9 | 50 | Y | 19.8 |
| 10 | 50 | Y | 17.5 |
| 11 | 50 | Y | 19.4 |
| 12 | 50 | Y | 12.0 |

[a] pmoles of RNA applied to a 100-µl column volume of SP-Sepharose (80 µM SP).
[b] Whether a thiopropyl-Sepharose column counterselection step was incorporated into the selection scheme prior to affinity selection on SP-Sepharose is indicated by either N (no) or Y (yes).
[c] Percentage of the applied RNA that was eluted with ten column volumes of SP binding buffer containing 100 mM DTT following an extensive wash with 20 column volumes of SP binding buffer.
[d] Results from a control experiment in which the initial random sequence RNA pool was applied to a thiopropyl-Sepharose column in the absence of substance P.

TABLE 2

Summary of SELEX experiment B selection cycle results.
Experiment B

| Selection cycle [a] | [SP] [b] | Counterselection column ? [c] | Percent eluted with DTT [d] |
| --- | --- | --- | --- |
| Ligand A13 [e] | 80 mM | N | 9.97 |
| 1 | 80 mM | N | 1.01 |
| 2 | 80 mM | N | 0.92 |
| 3 | 20 mM | N | 1.87 |
| 4 | 20 mM | N | 5.52 |
| 5 | 20 mM | N | 3.85 |
| 6 | 20 mM | N | 4.46 |
| 7 | 20 mM | N | 29.2 |
| 8 | 5.0 mM | Y | 16.3 |
| 9 | 2.5 mM | Y | 10.5 |
| 10 | 1.3 mM | Y | 8.00 |
| 11 | 1.3 mM | Y | 12.6 |
| 12 | 1.3 mM | Y | 14.4 |

[a] PCR mutagenesis of the ligand pool (of ligand A13 (SEQ ID NO:5) for selection cycle 1) preceded selection cycles 1–6; standard PCR amplification of the ligand pool preceded selection cycles 7–12.
[b] Concentration of substance P contained on the SP-Sepharose affinity matrix as a function of column volume (100 µl). Binding reactions occurred in well-mixed 1 ml suspensions.
[c] Whether a thiopropyl-Sepharose column counterselection step was incorporated into the selection scheme prior to affinity selection on SP-Sepharose is indicated by either N (no) or Y (yes).
[d] Percentage of the applied RNA that was eluted with 10 column volumes of SP binding buffer containing 100 mM DTT following an extensive wash with greater than 20 column volumes of SP binding buffer.
[e] Results from a control experiment with non-mutagenized ligand A13.

We claim:

1. A nucleic acid ligand to Substance P (SP) identified according to a process comprising the steps of:
   a) contacting a candidate mixture of nucleic acids with SP, wherein nucleic acids having an increased affinity to the SP relative to the candidate mixture may be partitioned from the remainder of the candidate mixture;
   b) partitioning the increased affinity nucleic acids from the remainder of the candidate mixture; and
   c) amplifying the increased affinity nucleic acids to yield a mixture of nucleic acids enriched in nucleic acids having increased affinity to SP, whereby a nucleic acid ligand of SP may be identified.

2. The nucleic acid ligand of claim 1 which is an RNA ligand, wherein the nucleotide sequence of said ligand is selected from the group consisting of the sequences set forth in FIGS. 2 and 3.

3. The RNA ligand of claim 2 wherein said ligand is selected from the group consisting of SEQ ID NOS:5, 18–21, 26–47 and 58.

4. The RNA ligand of claim 2 wherein said ligand is comprised of 2'-amino (2'-NH$_2$) modified nucleotides.

5. A purified and isolated non-naturally occurring nucleic acid ligand to SP.

6. The nucleic acid ligand of claim 5 which is an RNA ligand.

7. The nucleic acid ligand of claim 1 wherein said ligand comprises 2'-amino (2'-NH$_2$) modified nucleotides.

\* \* \* \* \*

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GCCGGATCCG  GGCCTCATGT  CGAANNNNNN  NNNNNNNNNN  NNNNNNNNNN      50

NNNNNNNNNN  NNNNNNNNNN  NNNNNNNNNN  NNNNTTGAGC  GTTTATTCTG     100
```

AGCTCCC 107

( 2 ) INFORMATION FOR SEQ ID NO:2:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCGAAGCTTA ATACGACTCA CTATAGGGAG CTCAGAATAA ACGCTCAA 48

( 2 ) INFORMATION FOR SEQ ID NO:3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCGGATCCG GGCCTCATGT CGAA 24

( 2 ) INFORMATION FOR SEQ ID NO:4:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGGAGCUCAG AAUAAACGCU CAANNNNNNN NNNNNNNNNN NNNNNNNNNN 50

NNNNNNNNNN NNNNNNNNNN NNNNNNNNNN NNNUUCGACA UGAGGCCCGG 100

AUCCGGC 107

( 2 ) INFORMATION FOR SEQ ID NO:5:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGAGCUCAG AAUAAACGCU CAAGGGCAAC GCGGGCACCC CGACAGGUGC 50

AAAAACGCAC CGACGCCCGG CCGAAGAAGG GGAUUCGACA UGAGGCCCGG 100

AUCCGGC 107

( 2 ) INFORMATION FOR SEQ ID NO:6:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:6:

Arg Pro Lys Pro Gln Gln Phe Phe Gly Leu Met
1             5                     10

( 2 ) INFORMATION FOR SEQ ID NO:7:

( i ) SEQUENCE CHARACTERISTICS:
    ( A ) LENGTH: 12
    ( B ) TYPE: amino acid
    ( C ) STRANDEDNESS: single
    ( D ) TOPOLOGY: linear ( x i ) SEQUENCE DESCRIPTION: SEQ ID NO:7:

```
Arg Pro Lys Pro Gln Gln Phe Phe Gly Leu Met Cys
1               5                   10
```

( 2 ) INFORMATION FOR SEQ ID NO:8:

( i ) SEQUENCE CHARACTERISTICS:
        ( A ) LENGTH: 12
        ( B ) TYPE: amino acid
        ( C ) STRANDEDNESS: single
        ( D ) TOPOLOGY: linear ( x i ) SEQUENCE DESCRIPTION: SEQ ID NO:8:

```
Cys Met Leu Gly Phe Phe Gln Gln Pro Lys Pro Arg
1               5                   10
```

( 2 ) INFORMATION FOR SEQ ID NO:9:

( i ) SEQUENCE CHARACTERISTICS:
        ( A ) LENGTH: 108
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | | | | | |
|---|---|---|---|---|---|
| GGGAGCUCAG | AAUAAACGCU | CAAGAACAAG | AUGGCAGUAA | CGCAACCCAG | 50 |
| ACAGGAAAAA | AACCCGACGC | GCAAAAACAA | CGGAUUCGAC | AUGAGGCCCG | 100 |
| GAUCCGGC | | | | | 108 |

( 2 ) INFORMATION FOR SEQ ID NO:10:

( i ) SEQUENCE CHARACTERISTICS:
        ( A ) LENGTH: 109
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | | | | | |
|---|---|---|---|---|---|
| GGGAGCUCAG | AAUAAACGCU | CAAGAACAAG | AUGGCAGUGA | CGCAACCCAG | 50 |
| ACAGGAAAAA | AACCCGACGC | GCAAAAAACA | ACGGAUUCGA | CAUGAGGCCC | 100 |
| GGAUCCGGC | | | | | 109 |

( 2 ) INFORMATION FOR SEQ ID NO:11:

( i ) SEQUENCE CHARACTERISTICS:
        ( A ) LENGTH: 111
        ( B ) TYPE: nucleic acid
        ( C ) STRANDEDNESS: single
        ( D ) TOPOLOGY: linear ( x i ) SEQUENCE DESCRIPTION: SEQ ID NO:11:

| | | | | | |
|---|---|---|---|---|---|
| GGGAGCUCAG | AAUAAACGCU | CAAGAACAAG | AUGGCAAUAA | CGCAACCCAG | 50 |
| ACAGGAAAAA | AAACCCGAC | GCGCAAAAAA | CAACGGAUUC | GACAUGAGGC | 100 |
| CCGGAUCCGG | C | | | | 111 |

( 2 ) INFORMATION FOR SEQ ID NO:12:

( i ) SEQUENCE CHARACTERISTICS:

(A) LENGTH: 107
(B) TYPE: nucleic acid
(C) STRANDEDNESS: single
(D) TOPOLOGY: linear (xi) SEQUENCE DESCRIPTION: SEQ ID NO:12:

| GGGAGCUCAG | AAUAAACGCU | CAAGAAGCGA | AAACAGAGGC | GAGAGGAAAC | 50 |
| CUAAAACAGC | GACGAAGCGG | CCACUGGUAU | CUCUUCGACA | UGAGGCCCGG | 100 |
| AUCCGGC | | | | | 107 |

(2) INFORMATION FOR SEQ ID NO:13:

(i) SEQUENCE CHARACTERISTICS:
(A) LENGTH: 107
(B) TYPE: nucleic acid
(C) STRANDEDNESS: single
(D) TOPOLOGY: linear (xi) SEQUENCE DESCRIPTION: SEQ ID NO:13:

| GGGAGCUCAG | AAUAAACGCU | CAAGAAGCGA | AAACAGAGGC | GAGAGGAAAC | 50 |
| CUAAAACAGC | GACGAAGUGG | CCACUGGUAU | CUCUUCGACA | UGAGGCCCGG | 100 |
| AUCCGGC | | | | | 107 |

(2) INFORMATION FOR SEQ ID NO:14:

(i) SEQUENCE CHARACTERISTICS:
(A) LENGTH: 107
(B) TYPE: nucleic acid
(C) STRANDEDNESS: single
(D) TOPOLOGY: linear (xi) SEQUENCE DESCRIPTION: SEQ ID NO:14:

| GGGAGCUCAG | AAUAAACGCU | CAAGAAGCGA | AGACAGAGGC | GAGAGGAAAC | 50 |
| CUAAAACAGC | GACGAAGUGG | CCACUGGUAU | CUCUUCGACA | UGAGGCCCGG | 100 |
| AUCCGGC | | | | | 107 |

(2) INFORMATION FOR SEQ ID NO:15:

(i) SEQUENCE CHARACTERISTICS:
(A) LENGTH: 107
(B) TYPE: nucleic acid
(C) STRANDEDNESS: single
(D) TOPOLOGY: linear (xi) SEQUENCE DESCRIPTION: SEQ ID NO:15:

| GGGAGCUCAG | AAUAAACGCU | CAAGAAGUGA | AAACAGAGGC | GAGAGGAAAC | 50 |
| CUAAAACAGC | GACGAAGCGG | CCACUGGUAU | CUCUUCGACA | UGAGGCCCGG | 100 |
| AUCCGGC | | | | | 107 |

(2) INFORMATION FOR SEQ ID NO:16:

(i) SEQUENCE CHARACTERISTICS:
(A) LENGTH: 107
(B) TYPE: nucleic acid
(C) STRANDEDNESS: single
(D) TOPOLOGY: linear (xi) SEQUENCE DESCRIPTION: SEQ ID NO:16:

| GGGAGCUCAG | AAUAAACGCU | CAAGAAGAGA | AAACAGAGGC | GAGAGGAAAC | 50 |
| CUAAAACAGC | GACGAAGCGG | CCACUGGUAU | CUCUUCGACA | UGAGGCCCGG | 100 |
| AUCCGGC | | | | | 107 |

( 2 ) INFORMATION FOR SEQ ID NO:17:

( i ) SEQUENCE CHARACTERISTICS:
    ( A ) LENGTH: 107
    ( B ) TYPE: nucleic acid
    ( C ) STRANDEDNESS: single
    ( D ) TOPOLOGY: linear ( x i ) SEQUENCE DESCRIPTION: SEQ ID NO:17:

| | | | | | |
|---|---|---|---|---|---|
| GGGAGCUCAG | AAUAAACGCU | CAAGAACCGA | AAACAGAGGC | GAGAGGAAAC | 50 |
| CUAAAACAGC | GACGAAGCGG | CCACUGGUAU | CUCUUCGACA | UGAGGCCCGG | 100 |
| AUCCGGC | | | | | 107 |

( 2 ) INFORMATION FOR SEQ ID NO:18:

( i ) SEQUENCE CHARACTERISTICS:
    ( A ) LENGTH: 106
    ( B ) TYPE: nucleic acid
    ( C ) STRANDEDNESS: single
    ( D ) TOPOLOGY: linear ( x i ) SEQUENCE DESCRIPTION: SEQ ID NO:18:

| | | | | | |
|---|---|---|---|---|---|
| GGGAGCUCAG | AAUAAACGCU | CAACGCACGA | CGCACCGUUA | CAGGGGGGA | 50 |
| AGAACCAACC | CGAGCGCACG | ACGGACCGAC | GCUUCGACAU | GAGGCCCGGA | 100 |
| UCCGGC | | | | | 106 |

( 2 ) INFORMATION FOR SEQ ID NO:19:

( i ) SEQUENCE CHARACTERISTICS:
    ( A ) LENGTH: 106
    ( B ) TYPE: nucleic acid
    ( C ) STRANDEDNESS: single
    ( D ) TOPOLOGY: linear ( x i ) SEQUENCE DESCRIPTION: SEQ ID NO:19:

| | | | | | |
|---|---|---|---|---|---|
| GGGAGCUCAG | AAUAAACGCU | CAACGCACGA | CGCACCGUUA | CAGGGGGGA | 50 |
| AAAGCCAACC | CGAGCGCACG | ACGGACCGAC | GCUUCGACAU | GAGGCCCGGA | 100 |
| UCCGGC | | | | | 106 |

( 2 ) INFORMATION FOR SEQ ID NO:20:

( i ) SEQUENCE CHARACTERISTICS:
    ( A ) LENGTH: 107
    ( B ) TYPE: nucleic acid
    ( C ) STRANDEDNESS: single
    ( D ) TOPOLOGY: linear ( x i ) SEQUENCE DESCRIPTION: SEQ ID NO:20:

| | | | | | |
|---|---|---|---|---|---|
| GGGAGCUCAG | AAUAAACGCU | CAACGCACGA | CGCACCGUUA | CAGGGGGGA | 50 |
| AAAAGCCAAC | CCGAGCGCAC | GACGGACCGA | CGCUUCGACA | UGAGGCCCGG | 100 |
| AUCCGGC | | | | | 107 |

( 2 ) INFORMATION FOR SEQ ID NO:21:

( i ) SEQUENCE CHARACTERISTICS:
    ( A ) LENGTH: 107
    ( B ) TYPE: nucleic acid
    ( C ) STRANDEDNESS: single
    ( D ) TOPOLOGY: linear ( x i ) SEQUENCE DESCRIPTION: SEQ ID NO:21:

```
GGGAGCUCAG  AAUAAACGCU  CAAAGGGCAA  CGCGGGCACC  CCGACAGGUG           50

CAAAACGCAC  CGACGCCCGG  CCGAAGAAGG  GGAUUCGACA  UGAGGCCCGG          100

AUCCGGC                                                             107
```

( 2 ) INFORMATION FOR SEQ ID NO:22:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GGGAGCUCAG  AAUAAACGCU  CAAGCGAAAA  GACGAAAAAA  CCGACGACAC           50

UAGCGCGAUU  CGGAAGACUA  GCAACAACGA  CACUUCGACA  UGAGGCCCGG          100

AUCCGGC                                                             107
```

( 2 ) INFORMATION FOR SEQ ID NO:23:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GGGAGCUCAG  AAUAAACGCU  CAAAAGGAAG  AAAACAGCAU  AAUUAGGCAA           50

AAAGACAAAA  ACAACAAAUA  AAGAAAGAGC  AUAUUCGACA  UGAGGCCCGG          100

AUCCGGC                                                             107
```

( 2 ) INFORMATION FOR SEQ ID NO:24:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GGGAGCUCAG  AAUAAACGCU  CAAACAAAAA  ACAAACGAAA  ACAUAAAAAU           50

AAAAUUAAAG  UAGAAGCGCA  AAGAUUAUUA  CAAUUCGACA  UGAGGCCCGG          100

AUCCGGC                                                             107
```

( 2 ) INFORMATION FOR SEQ ID NO:25:

( i ) SEQUENCE CHARACTERISTICS:
        ( A ) LENGTH: 108
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GGGAGCUCAG  AAUAAACGCU  CAAAACUCAA  UAUAAAGAAA  ACGACAAAAC           50

AGAAUGAAGC  CAAGAAAACA  UACAAGAACG  AAGCUUCGAC  AUGAGGCCCG          100

GAUCCGGC                                                            108
```

( 2 ) INFORMATION FOR SEQ ID NO:26:

( i ) SEQUENCE CHARACTERISTICS:
        ( A ) LENGTH: 106
        ( B ) TYPE: nucleic acid (C) STRANDEDNESS: single
(D) TOPOLOGY: linear (xi) SEQUENCE DESCRIPTION: SEQ ID NO:26:

| | | | | |
|---|---|---|---|---|
| GGGAGCUCAG | AAUAAACGCU | CAACAAGCAA | GGCAAUGCAA | ACCCUUAGGU | 50
| CACAAGAACC | GAUGAGGCUG | UCCGGCACUU | CAUUCGACAU | GAGGCCCGGA | 100
| UCCGGC | | | | | 106

(2) INFORMATION FOR SEQ ID NO:27:

(i) SEQUENCE CHARACTERISTICS:
        (A) LENGTH: 107
        (B) TYPE: nucleic acid
        (C) STRANDEDNESS: single
        (D) TOPOLOGY: linear (xi) SEQUENCE DESCRIPTION: SEQ ID NO:27:

| | | | | |
|---|---|---|---|---|
| GGGAGCUCAG | AAUAAACGCU | CAACCAAACU | AGGCUAUGGA | AACCCUAAGG | 50
| CUAAUAAAGC | CAAUGACGCC | AUCCAGGUAC | UUCUUCGACA | UGAGGCCCGG | 100
| AUCCGGC | | | | | 107

(2) INFORMATION FOR SEQ ID NO:28:

(i) SEQUENCE CHARACTERISTICS:
        (A) LENGTH: 107
        (B) TYPE: nucleic acid
        (C) STRANDEDNESS: single
        (D) TOPOLOGY: linear (xi) SEQUENCE DESCRIPTION: SEQ ID NO:28:

| | | | | |
|---|---|---|---|---|
| GGGAGCUCAG | AAUAAACGCU | CAAGAGACCU | GGCAAUCGAA | ACCCUAAGGA | 50
| UACAUAAUCC | AAUGAGACCA | UCCGGUCACU | UCAUUCGACA | UGAGGCCCGG | 100
| AUCCGGC | | | | | 107

(2) INFORMATION FOR SEQ ID NO:29:

(i) SEQUENCE CHARACTERISTICS:
        (A) LENGTH: 105
        (B) TYPE: nucleic acid
        (C) STRANDEDNESS: single
        (D) TOPOLOGY: linear (xi) SEQUENCE DESCRIPTION: SEQ ID NO:29:

| | | | | |
|---|---|---|---|---|
| GGGAGCUCAG | AAUAAACGCU | CAACGCUCCG | GCAGUAGAAA | CCCUAAGGUU | 50
| AUUAGACCAA | UGAUGCCAUC | CGGCCACAAC | UUUCGACAUG | AGGCCCGGAU | 100
| CCGGC | | | | | 105

(2) INFORMATION FOR SEQ ID NO:30:

(i) SEQUENCE CHARACTERISTICS:
        (A) LENGTH: 106
        (B) TYPE: nucleic acid
        (C) STRANDEDNESS: single
        (D) TOPOLOGY: linear (xi) SEQUENCE DESCRIPTION: SEQ ID NO:30:

| | | | | |
|---|---|---|---|---|
| GGGAGCUCAG | AAUAAACGCU | CAACCUCCUG | GCAGUAGAAA | CCCUAAGGUC | 50
| AUUACGACCA | AUGAUGCUAU | CCAGGUACUU | CAUUCGACAU | GAGGCCCGGA | 100
| UCCGGC | | | | | 106

( 2 ) INFORMATION FOR SEQ ID NO:31:

( i ) SEQUENCE CHARACTERISTICS:
        ( A ) LENGTH: 106
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
GGGAGCUCAG  AAUAAACGCU  CAACGCUCCU  GGCUGUGGAA  ACCCUUAGGU        50
ACAAAAACCA  AUGACGCCAU  CUGGACAAUU  CAUUCGACAU  GAGGCCCGGA       100
UCCGGC                                                           106
```

( 2 ) INFORMATION FOR SEQ ID NO:32:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
GGGAGCUCAG  AAUAAACGCU  CAACCAACCA  GGCUAUGGAA  ACCCUUAGGU        50
UAUAACAACC  AAUGACGCCG  UCCAGGUUCA  UCUUUCGACA  UGAGGCCCGG       100
AUCCGGC                                                          107
```

( 2 ) INFORMATION FOR SEQ ID NO:33:

( i ) SEQUENCE CHARACTERISTICS:
        ( A ) LENGTH: 106
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
GGGAGCUCAG  AAUAAACGCU  CAACAGCAAG  GCUAUAGAAA  CCCUUAGGUC        50
AUAAAGACCA  AUGAUGCCUU  CCAGGUUCUU  CUUUCGACAU  GAGGCCCGGA       100
UCCGGC                                                           106
```

( 2 ) INFORMATION FOR SEQ ID NO:34:

( i ) SEQUENCE CHARACTERISTICS:
        ( A ) LENGTH: 106
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
GGGAGCUCAG  AAUAAACGCU  CAACGUACCG  GCAAUCGAAA  CCCUAAGGUU        50
ACAUAAACCA  AUGAGGCCGC  ACGGUCACUU  CAUUCGACAU  GAGGCCCGGA       100
UCCGGC                                                           106
```

( 2 ) INFORMATION FOR SEQ ID NO:35:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:35:

```
GGGAGCUCAG  AAUAAACGCU  CAAGAGACCA  GGCUGAUGAA  ACCCUUAGGC        50
```

UUAAUAACCA AUGAUGCCAU CCGGCAUACU UCAUUCGACA UGAGGCCCGG    100

AUCCGGC    107

( 2 ) INFORMATION FOR SEQ ID NO:36:

( i ) SEQUENCE CHARACTERISTICS:
        ( A ) LENGTH: 108
        ( B ) TYPE: nucleic acid
        ( C ) STRANDEDNESS: single
        ( D ) TOPOLOGY: linear ( x i ) SEQUENCE DESCRIPTION: SEQ ID NO:36:

GGGAGCUCAG AAUAAACGCU CAACUUCCAA GGCAGUGGAA ACCCUAAGGU    50

CAAUAAUGAC CAAUGACGCC GCUCCGGUUC AACCUUCGAC AUGAGGCCCG    100

GAUCCGGC    108

( 2 ) INFORMATION FOR SEQ ID NO:37:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGGAGCUCAG AAUAAACGCU CAAGAGACCC GGCAAUAGAA ACCCUUAGGA    50

CACAAAGUCC AAUGAUGCCG UCCACAUACU UCAUUCGACA UGAGGCCCGG    100

AUCCGGC    107

( 2 ) INFORMATION FOR SEQ ID NO:38:

( i ) SEQUENCE CHARACTERISTICS:
        ( A ) LENGTH: 105
        ( B ) TYPE: nucleic acid
        ( C ) STRANDEDNESS: single
        ( D ) TOPOLOGY: linear ( x i ) SEQUENCE DESCRIPTION: SEQ ID NO:38:

GGGAGCUCAG AAUAAACGCU CAACUCUGGG CUAUCGAAAC CCUUAGGAUA    50

CAAAAUCCAA UGAGGCCGAC CGGUAACAUU CUUCGACAUG AGGCCCGGAU    100

CCGGC    105

( 2 ) INFORMATION FOR SEQ ID NO:39:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGGAGCUCAG AAUAAACGCU CAAAGUUCCU GGCAGUAGAA ACCCUAAGGU    50

CACUUAGACC AAUGAAGCCU UCCGGUUAUA UCAUUCGACA UGAGGCCCGG    100

AUCCGGC    107

( 2 ) INFORMATION FOR SEQ ID NO:40:

( i ) SEQUENCE CHARACTERISTICS:
        ( A ) LENGTH: 108
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGGAGCUCAG AAUAAACGCU CAAACAUACC CGGCGAUCGA AACCCUUAGG        50

UUACAUAAAC CAAUGAGGCC GUCCGGACAC AUAAUUCGAC AUGAGGCCCG        100

GAUCCGGC        108

( 2 ) INFORMATION FOR SEQ ID NO:41:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:41:

GGGAGCUCAG AAUAAACGCU CAACUCCCAA GGCAAUGGAA ACCCUUAGGU        50

UACUACAACC GAUGACGCCA CCCAGGUACU UCAUUCGACA UGAGGCCCGG        100

AUCCGGC        107

( 2 ) INFORMATION FOR SEQ ID NO:42:

( i ) SEQUENCE CHARACTERISTICS:
        ( A ) LENGTH: 107
        ( B ) TYPE: nucleic acid
        ( C ) STRANDEDNESS: single
        ( D ) TOPOLOGY: linear ( x i ) SEQUENCE DESCRIPTION: SEQ ID NO:42:

GGGAGCUCAG AAUAAACGCU CAAUGUUCCU GGCAAUAGAA ACCCUUAGGU        50

UAUAAAGACC AAUGAUGCCA UCCGGCUACU UUGUUCGACA UGAGGCCCGG        100

AUCCGGC        107

( 2 ) INFORMATION FOR SEQ ID NO:43:

( i ) SEQUENCE CHARACTERISTICS:
        ( A ) LENGTH: 104
        ( B ) TYPE: nucleic acid
        ( C ) STRANDEDNESS: single
        ( D ) TOPOLOGY: linear ( x i ) SEQUENCE DESCRIPTION: SEQ ID NO:43:

GGGAGCUCAG AAUAAACGCU CAACUCCUGG CAGUAAAAAC CCUUAGGAAG        50

CGAUUCCAAU GAAGCCAUCC GGUUACUUCU UUCGACAUGA GGCCCGGAUC        100

CGGC        104

( 2 ) INFORMATION FOR SEQ ID NO:44:

( i ) SEQUENCE CHARACTERISTICS:
        ( A ) LENGTH: 104
        ( B ) TYPE: nucleic acid
        ( C ) STRANDEDNESS: single
        ( D ) TOPOLOGY: linear ( x i ) SEQUENCE DESCRIPTION: SEQ ID NO:44:

GGGAGCUCAG AAUAAACGCU CAAACAAGGC AAUAGAAACC CUUAGGUUGU        50

UACAACCAAU GAUGCCAUUC GGUCACUUCA UUCGACAUGA GGCCCGGAUC        100

CGGC        104

( 2 ) INFORMATION FOR SEQ ID NO:45:

5,637,682

( i ) SEQUENCE CHARACTERISTICS:
 ( A ) LENGTH: 107
 ( B ) TYPE: nucleic acid
 ( C ) STRANDEDNESS: single
 ( D ) TOPOLOGY: linear ( x i ) SEQUENCE DESCRIPTION: SEQ ID NO:45:

| | | | | | |
|---|---|---|---|---|---|
| GGGAGCUCAG | AAUAAACGCU | CAACUUCCGA | GGCAAUAGAA | ACCCUAAGGC | 50 |
| UUAAACAACC | AAUGAUGCCA | UCCAGGCAAG | UCAUUCGACA | UGAGGCCCGG | 100 |
| AUCCGGC | | | | | 107 |

( 2 ) INFORMATION FOR SEQ ID NO:46:

( i ) SEQUENCE CHARACTERISTICS:
 ( A ) LENGTH: 107
 ( B ) TYPE: nucleic acid
 ( C ) STRANDEDNESS: single
 ( D ) TOPOLOGY: linear ( x i ) SEQUENCE DESCRIPTION: SEQ ID NO:46:

| | | | | | |
|---|---|---|---|---|---|
| GGGAGCUCAG | AAUAAACGCU | CAAAAGCAA | GGCUAUCGAA | ACCCUAAGGG | 50 |
| UGCAAACCCA | AUGAGGCCUU | UCCGGGAACC | UAAUUCGACA | UGAGGCCCGG | 100 |
| AUCCGGC | | | | | 107 |

( 2 ) INFORMATION FOR SEQ ID NO:47:

( i ) SEQUENCE CHARACTERISTICS:
 ( A ) LENGTH: 107
 ( B ) TYPE: nucleic acid
 ( C ) STRANDEDNESS: single
 ( D ) TOPOLOGY: linear ( x i ) SEQUENCE DESCRIPTION: SEQ ID NO:47:

| | | | | | |
|---|---|---|---|---|---|
| GGGAGCUCAG | AAUAAACGCU | CAACUUCCAA | GGCAAUAGAA | ACCCUUAGGA | 50 |
| UACAAGUUCC | GAUGAAGCCA | CCCGGUCUCG | UCAUUCGACA | UGAGGCCCGG | 100 |
| AUCCGGC | | | | | 107 |

( 2 ) INFORMATION FOR SEQ ID NO:48:

( i ) SEQUENCE CHARACTERISTICS:
 ( A ) LENGTH: 108
 ( B ) TYPE: nucleic acid
 ( C ) STRANDEDNESS: single
 ( D ) TOPOLOGY: linear ( x i ) SEQUENCE DESCRIPTION: SEQ ID NO:48:

| | | | | | |
|---|---|---|---|---|---|
| GGGAGCUCAG | AAUAAACGCU | CAAAAAACAG | GACACCAUGA | UAAAUGGACG | 50 |
| AGUUCACUGG | AGCGUCUAAA | AGGGCACCCU | UGGAUUCGAC | AUGAGGCCCG | 100 |
| GAUCCGGC | | | | | 108 |

( 2 ) INFORMATION FOR SEQ ID NO:49:

( i ) SEQUENCE CHARACTERISTICS:
 ( A ) LENGTH: 107
 ( B ) TYPE: nucleic acid
 ( C ) STRANDEDNESS: single
 ( D ) TOPOLOGY: linear ( x i ) SEQUENCE DESCRIPTION: SEQ ID NO:49:

| | | | | | |
|---|---|---|---|---|---|
| GGGAGCUCAG | AAUAAACGCU | CAAUAACAGG | ACACCAUGAU | UAAUGGACGA | 50 |
| GUUCACUAGG | GCGGUUAAAA | GAGCUCUCGA | GGAUUCGACA | UGAGGCCCGG | 100 |

AUCCGGC                                                                                                    107

( 2 ) INFORMATION FOR SEQ ID NO:50:

( i ) SEQUENCE CHARACTERISTICS:
  ( A ) LENGTH: 107
  ( B ) TYPE: nucleic acid
  ( C ) STRANDEDNESS: single
  ( D ) TOPOLOGY: linear ( x i ) SEQUENCE DESCRIPTION: SEQ ID NO:50:

GGGAGCUCAG AAUAAACGCU CAAGAACAGG ACACCAAGAU AAUUGGACGA        50

GUUUACUAGG GCGGCUAUGC UGGCUCUCGA GGAUUCGACA UGAGGCCCGG        100

AUCCGGC                                                      107

( 2 ) INFORMATION FOR SEQ ID NO:51:

( i ) SEQUENCE CHARACTERISTICS:
  ( A ) LENGTH: 107
  ( B ) TYPE: nucleic acid
  ( C ) STRANDEDNESS: single
  ( D ) TOPOLOGY: linear ( x i ) SEQUENCE DESCRIPTION: SEQ ID NO:51:

GGGAGCUCAG AAUAAACGCU CAAGAACAGG ACACCUGGUU CUCAGGACGA        50

GUUUACUAGG GCGGCAAAAA GGGCUCUCGU GGGUUCGACA UGAGGCCCGG        100

AUCCGGC                                                      107

( 2 ) INFORMATION FOR SEQ ID NO:52:

( i ) SEQUENCE CHARACTERISTICS:
  ( A ) LENGTH: 107
  ( B ) TYPE: nucleic acid
  ( C ) STRANDEDNESS: single
  ( D ) TOPOLOGY: linear ( x i ) SEQUENCE DESCRIPTION: SEQ ID NO:52:

GGGAGCUCAG AAUAAACGCU CAAAAACAGG ACACCAAUUU UAUUGGACGA        50

GUUUACUAGG GCGGUAUUAU GGGCUCGCGA GGAUUCGACA UGAGGCCCGG        100

AUCCGGC                                                      107

( 2 ) INFORMATION FOR SEQ ID NO:53:

( i ) SEQUENCE CHARACTERISTICS:
  ( A ) LENGTH: 106
  ( B ) TYPE: nucleic acid
  ( C ) STRANDEDNESS: single
  ( D ) TOPOLOGY: linear ( x i ) SEQUENCE DESCRIPTION: SEQ ID NO:53:

GGGAGCUCAG AAUAAACGCU CAAAAACAGG ACACCAUGAA AAUGGACGAG        50

UUCACUAGAG CGUUGAGCUG UGCGCCCGUG GAUUCGACAU GAGGCCCGGA        100

UCCGGC                                                       106

( 2 ) INFORMATION FOR SEQ ID NO:54:

( i ) SEQUENCE CHARACTERISTICS:
  ( A ) LENGTH: 106
  ( B ) TYPE: nucleic acid
  ( C ) STRANDEDNESS: single
  ( D ) TOPOLOGY: linear ( x i ) SEQUENCE DESCRIPTION: SEQ ID NO:54:

(2) INFORMATION FOR SEQ ID NO:54:

(i) SEQUENCE CHARACTERISTICS:
(A) LENGTH: (continued)
(B) TYPE: nucleic acid
(C) STRANDEDNESS: single
(D) TOPOLOGY: linear (xi) SEQUENCE DESCRIPTION: SEQ ID NO:54:

| | | | | | |
|---|---|---|---|---|---|
| GGGAGCUCAG | AAUAAACGCU | CAAAAACAGG | ACACCAAGAU | UAUUGGACGA | 50 |
| GUUUACUAGG | GCGAUUAAUG | GGCUCGCGAU | GAUUCGACAU | GAGGCCCGGA | 100 |
| UCCGGC | | | | | 106 |

(2) INFORMATION FOR SEQ ID NO:55:

(i) SEQUENCE CHARACTERISTICS:
(A) LENGTH: 104
(B) TYPE: nucleic acid
(C) STRANDEDNESS: single
(D) TOPOLOGY: linear (xi) SEQUENCE DESCRIPTION: SEQ ID NO:55:

| | | | | | |
|---|---|---|---|---|---|
| GGGAGCUCAG | AAUAAACGCU | CAAACAGGA | CACCUUGAAU | AAAGGACGAG | 50 |
| UUUACUGUGC | GUUUAGUAGA | GAACCCGGGA | UUCGACAUGA | GGCCCGGAUC | 100 |
| CGGC | | | | | 104 |

(2) INFORMATION FOR SEQ ID NO:56:

(i) SEQUENCE CHARACTERISTICS:
(A) LENGTH: 105
(B) TYPE: nucleic acid
(C) STRANDEDNESS: single
(D) TOPOLOGY: linear (xi) SEQUENCE DESCRIPTION: SEQ ID NO:56:

| | | | | | |
|---|---|---|---|---|---|
| GGGAGCUCAG | AAUAAACGCU | CAAGCUCAAG | GCAGAAACAG | GACACACCAA | 50 |
| GACGAGUUAA | CCAGCCCAGC | UUGACCAUAC | AUUCGACAUG | AGGCCCGGAU | 100 |
| CCGGC | | | | | 105 |

(2) INFORMATION FOR SEQ ID NO:57:

(i) SEQUENCE CHARACTERISTICS:
(A) LENGTH: 106
(B) TYPE: nucleic acid
(C) STRANDEDNESS: single
(D) TOPOLOGY: linear (xi) SEQUENCE DESCRIPTION: SEQ ID NO:57:

| | | | | | |
|---|---|---|---|---|---|
| GGGAGCUCAG | AAUAAACGCU | CAAAAGGUAA | GAAACAGGAC | ACGCACUUAA | 50 |
| ACAGACGAGU | UAACCAUACC | UAGAUCGCGG | AAUUCGACAU | GAGGCCCGGA | 100 |
| UCCGGC | | | | | 106 |

(2) INFORMATION FOR SEQ ID NO:58:

(i) SEQUENCE CHARACTERISTICS:
(A) LENGTH: 107
(B) TYPE: nucleic acid
(C) STRANDEDNESS: single
(D) TOPOLOGY: linear (xi) SEQUENCE DESCRIPTION: SEQ ID NO:58:

| | | | | | |
|---|---|---|---|---|---|
| GGGAGCUCAG | AAUAAACGCU | CAAAAAGGCA | CUGACCACCC | UCAGGAAGAA | 50 |
| UAACCGCGGU | CACCCGCAUC | CGAGUCUAUC | AAUUUCGACA | UGAGGCCCGG | 100 |
| AUCCGGC | | | | | 107 |

(2) INFORMATION FOR SEQ ID NO:59:

(i) SEQUENCE CHARACTERISTICS:
(A) LENGTH: 36

(B) TYPE: nucleic acid
(C) STRANDEDNESS: single
(D) TOPOLOGY: linear (xi) SEQUENCE DESCRIPTION: SEQ ID NO:59:

WRUNGAAACC CUWAGGN YRN WWVDNCCRAU GANGCC    36

(2) INFORMATION FOR SEQ ID NO:60:

(i) SEQUENCE CHARACTERISTICS:
(A) LENGTH: 47
(B) TYPE: nucleic acid
(C) STRANDEDNESS: single
(D) TOPOLOGY: linear (xi) SEQUENCE DESCRIPTION: SEQ ID NO:60:

CGCUCAADAA CAGGACACCW DKWWHWHWGG ACGAGUU YAC URGDGCG    47

(2) INFORMATION FOR SEQ ID NO:61:

(i) SEQUENCE CHARACTERISTICS:
(A) LENGTH: 5
(B) TYPE: amino acid
(C) STRANDEDNESS: single
(D) TOPOLOGY: linear (ix) FEATURE:
(A) NAME/KEY: Xaa
(B) LOCATION: 2
(C) OTHER INFORMATION: AROMATIC OR ALIPHATIC AMINO ACID (xi) SEQUENCE DESCRIPTION: SEQ ID NO:61:

Phe Xaa Gly Leu Met
1               5

(2) INFORMATION FOR SEQ ID NO:62:

(i) SEQUENCE CHARACTERISTICS:
(A) LENGTH: 19
(B) TYPE: nucleic acid
(C) STRANDEDNESS: single
(D) TOPOLOGY: linear (xi) SEQUENCE DESCRIPTION: SEQ ID NO:62:

GGCNNNNNNN ACCCUNAGG    19

(2) INFORMATION FOR SEQ ID NO:63:

(i) SEQUENCE CHARACTERISTICS:
(A) LENGTH: 4
(B) TYPE: amino acid
(C) STRANDEDNESS: single
(D) TOPOLOGY: linear (xi) SEQUENCE DESCRIPTION: SEQ ID NO:63:

Phe Gly Leu Met (2) INFORMATION FOR SEQ ID NO:64:

(i) SEQUENCE CHARACTERISTICS:
(A) LENGTH: 4
(B) TYPE: amino acid
(C) STRANDEDNESS: single
(D) TOPOLOGY: linear (xi) SEQUENCE DESCRIPTION: SEQ ID NO:64:

Arg Pro Lys Pro ( 2 ) INFORMATION FOR SEQ ID NO:65:

( i ) SEQUENCE CHARACTERISTICS:
      ( A ) LENGTH: 5
      ( B ) TYPE: amino acid
      ( C ) STRANDEDNESS: single
      ( D ) TOPOLOGY: linear ( x i ) SEQUENCE DESCRIPTION: SEQ ID NO:65:

Pro  Gln  Gln  Phe  Phe
1                    5

( 2 ) INFORMATION FOR SEQ ID NO:66:

( i ) SEQUENCE CHARACTERISTICS:
      ( A ) LENGTH: 36
      ( B ) TYPE: nucleic acid
      ( C ) STRANDEDNESS: single
      ( D ) TOPOLOGY: linear ( x i ) SEQUENCE DESCRIPTION: SEQ ID NO:66:

CGUGUCCCCC  ACUCGAGAUA  UUCGACAUGA  GACACG                     3 6